United States Patent [19]

Kitaguchi et al.

[11] Patent Number: 5,436,221
[45] Date of Patent: Jul. 25, 1995

[54] TUMOR METASTASIS INHIBITING COMPOUNDS AND METHODS

[75] Inventors: Hiroshi Kitaguchi; Hiroyuki Komazawa; Masayoshi Kojima; Hideto Mori; Naoyuki Nishikawa; Hideaki Satoh; Atsushi Orikasa; Mitsunori Ono, all of Minami-Ashigara; Ichiro Azuma; Ikuo Saiki, both of Sapporo, all of Japan

[73] Assignee: Fuji Photo Film Co., Ltd., Kanagawa, Japan

[21] Appl. No.: 834,848

[22] Filed: Feb. 13, 1992

[30] Foreign Application Priority Data

Feb. 14, 1991 [JP] Japan .................. 3-040860
Nov. 13, 1991 [JP] Japan .................. 3-297482
Feb. 7, 1992 [JP] Japan .................. 4-022799

[51] Int. Cl.$^6$ .......... A61K 38/00; C07K 5/00; C07K 7/00; C07K 14/00
[52] U.S. Cl. .................. 514/12; 514/13; 514/14; 514/15; 514/16; 514/17; 514/18; 530/324; 530/325; 530/326; 530/327; 530/328; 530/337; 530/330; 530/331
[58] Field of Search ............... 530/324, 330, 326, 329, 530/327, 328, 331; 514/15, 14, 13, 16, 17, 18, 12

[56] References Cited

U.S. PATENT DOCUMENTS

4,505,853  3/1985  Goldstein et al. .................. 530/301

FOREIGN PATENT DOCUMENTS

0266513   6/1987  European Pat. Off. ....... C07K 5/00
0347931  12/1989  European Pat. Off.
9005177   5/1990  WIPO
9108220   6/1991  WIPO
9117173  11/1991  WIPO

OTHER PUBLICATIONS

Mazerolles et al, *Cell*, vol. 55, No. 3, 1988, pp. 497–504.
Piatier-Tonneau et al., *PNAS*, vol. 88, 8/91, pp. 6858–6862.
Cell, vol. 55, No. 3, Nov. 4, 1988, pp. 497–504, Cambridge, Mass., US; F. Mazerolles et al. "Immunosuppressive properties of synthetic peptides derived from CD4 and HLA-DR antigens".
Proceedings of the National Academy of Sciences, USA, vol. 81, No. 19, Oct. 1984, pp. 5985–5988; M. D. Pierschbacher et al.: "Variants of the cell recognition site of fibronectin that retain attachment-promoting activity".
The Journal of Biological Chemistry, Vo. 264, No. 22, Aug. 5, 1989, pp. 13102–13108, The American Society for Biochemistry and Molecular Biology, Inc., US: B. Steiner et al.: "Ca$^{2+}$—dependent binding of a synthetic Arg-Gly-Asp (RDG) peptide to a single site on the purified platelet glycoprotein IIb-IIIa complex".

(List continued on next page.)

*Primary Examiner*—Jill Warden
*Assistant Examiner*—A. M. Davenport
*Attorney, Agent, or Firm*—Sughrue, Mion, Zinn, Macpeak & Seas

[57] ABSTRACT

A peptide derivative containing 1 to 20 units of peptide unit represented by the following general formula [I] or a pharmaceutically acceptable salt thereof;

$$[Z]-Arg-X-Asp-[Y] \qquad [I]$$

wherein Arg represents L- or D-arginine residue, Asp represents L-aspartic acid residue, X represents L- or D-leucine, D-isoleucine, L- or D-norleucine, L- or D-phenylalanine, D-phenylglycine or D-alanine residue, and [Z] and [Y] each represents an amino acid or a peptide residue, which may be present or absent, selected from glycine, L-serine, L-threonine, L- and D-aspartic acid, L-alanine, L- and D-glutamic acid, L-proline residues and a peptide residue constituted by the foregoing amino acid residues, and a pharmaceutical composition comprising the peptide derivative. The composition of the present invention is useful as an agent for inhibiting tumor metastasis.

32 Claims, No Drawings

OTHER PUBLICATIONS

Hoppe-Seyler's Z. Physiol. Chem., vol. 364, Aug. 1983, pp. 933–940; L. Kisfaludy et al.: "Immuno-regulating peptides, I. Synthesis and structure-activity relationships of thymopentin analogs".

Chemical Abstracts, vol. 114, No. 9, Mar. 4, 1991, p. 481, Abstract No. 79202w, Columbus, Ohio, US.

J. B. Lawrence et al.: "Arginine-glycine-aspartic acid- and fibrinogen gamma-chain carboxyterminal peptides inhibit platelet adherence to arterial subendothelium at high wall shear rates: an effect dissociable from interference with adhesive protein binding", J. Clin. Invest. 1190, 86(5), 1715-22.

Chemical Abstracts, Vo. 113, No. 5, Jul. 30, 1990, p. 425, Abstract No. 38496f, Columbus, Ohio, US.

F. Mazerolles et al.: "Regulation of T helper-B lymphocyte adhesion trough CD4–HLA class II interaction", & Eur. J. Immunol. 1990, 20(3), 637–44.

Chemical Abstracts, vol. 109, No. 1, Jul. 4, 1988, p. 355, Abstract No. 3715s, Columbus, Ohio, US.

M. A. Quaissi et al.: "Fluorescence-activated cell-sorting analysis of fibronectin peptides binding to Trypasnosoma cruzi trypomastigotes", & J. Protozool. 1099, 35(1), 111-14.

Chemical Abstracts, vol. 105, No. 3, Jul. 21, 1986, p. 516, Abstract No. 22866a, Columbus, Ohio, US.

C. Auffray et al.: "Speculation on sequence homologies between the fibronectin cell-attachment site, major histocompatibility antigens, and a putative AIDS virus polypeptide", & Hum. Immunol. 1986, 15(4) 381-90.

TUMOR METASTASIS INHIBITING COMPOUNDS AND METHODS

BACKGROUND OF THE INVENTION

1. Field of the Invention

The present invention relates to a peptide derivative comprising a tripeptide unit or a pharmaceutically acceptable salt thereof as an essential constituent unit as well as a composition for inhibiting metastasis of tumor.

2. Prior Art

Fibronectin is a protein involved in the cell-extracellular substrate cohesion and is likewise thought to be involved in coagulation of blood platelets and the metastasis of tumor. These interactions are mediated by a series of receptors present in the cell surface region, it is confirmed that these receptors can specifically recognize an amino acid sequence: arginine-glycine-aspartic acid (hereinafter abbreviated as "Arg—Gly—Asp") of the fibronectin although the fibronectin is a macromolecule having a molecular weight of about 250,000, and there has been reported that the sequence plays an important role in the interaction between the receptors and the fibronectin (Nature, 309, 1984, p 30). The above tripeptide sequence, Arg—Gly—Asp, is present in other cohesive proteins such as vitronectin, and fibronectin associates with receptors of cells via the tripeptide sequence to transfer the information of fibronection to the adhered cells. Further, fibronectin is thought to have bonding ability to natural macromolecules such as heparin, collagen and fibrin and to be involved in adhesion of cells and interstitial connective tissue as well as differentiation and proliferation of cells.

Since the proteins having the cell adhesion activity have various biological activities as described above, there have been conducted many studies on the applications of these proteins for pharmaceutical drugs and materials. For example, there have been reported a method for inhibiting the coagulation of blood platelets by the use of various linear and cyclic oligopeptides having an Arg—Gly—Asp sequence (Polymer Preprints, Japan, 38, 1989, p. 3149; Japanese Unexamined Patent Publication (hereinafter referred to as "J. P. KOKAI") No. Hei 2-174797); a method in which a peptide having an Arg—Gly—Asp sequence is used as a cell movement-inhibiting agent (J. P. KOKAI No. Hei 2-4716); and a method using, as a cell-adhesive membrane, a PMMA film on which Arg—Gly—Asp sequences are immobilized (Polymer Preprints, Japan, 37, 1988, p. 705). In addition, J. P. KOKAI Nos. Hei 1-309682 and Hei 1-305960 disclose a method which comprises covalently bonding peptides having Arg—Gly—Asp sequences as essential structural units to a polymer and in which the resulting product is used as a substrate for cultivating animal cells or for biological composite artificial organs and J. P. KOKAI No. Sho 64-6217 discloses a method in which a polypeptide having Arg—Gly—Asp—Ser (SEQ ID NO.16) sequences is used as a platelet protective agent for blood taken out of the body.

Further, the cell-adhesive proteins have been paid attention as materials involved in metastasis of tumor. During the series of stages of the metastasis of tumor, tumor cells could contact with various host cells and biological macromolecules and, by the presence of the cell adhesive proteins such as fibronectin, the cells form cell coagulations to facilitate proliferation and survival of the tumor cells. In this regard, however, it is reported that if the adhesive core sequence of fibronectin, the tripeptide Arg—Gly—Asp, is present in such a circumstance, the tripeptide would associate with the receptors on the surface of the cells in a competitive manner with the cell adhesive proteins and thus may inhibit the metastasis of tumor (Science, 238 (1986) p 467). Further, there has been known a method comprising inhibiting the metastasis of tumor by the use of an oligopeptide having Arg—Gly—Asp sequences or a polypeptide having the sequence as repeating units (Int. J. Biol. Macromol., 11, 1989, p 23 ibid, 11, 1989, p. 226; and Jpn. J. Cancer Res., 60, 1989, p. 722).

As described above, many studies on the applications of the activities of the cell adhesive proteins such as fibronectin or peptide fragments thereof for pharmaceutical drugs and related medical materials have actively conducted, and the applications of the adhesive core sequence, Arg—Gly—Asp—Ser, (SEQ ID NO.16) to tumor metastasis inhibiting agents are particularly intensively conducted. However, according to the studies so far, the core sequence was regarded as essential for the expression of the biological activity mediated by the receptor and the ligand and it was reported that any peptide analog having another amino acid residue instead of any of the constituent amino acid residues, particularly the Arg residue, could not exhibit the activity .(:Polymer Preprints, Japan, 38 (1989) p 3149: J. Biol. Chem., 262 (1987) p 17294).

SUMMARY OF THE INVENTION

Accordingly, an object of the present invention is to provide a novel peptide derivative or pharmaceutically acceptable salt thereof, which exhibits enhanced ability for inhibiting metastasis of tumor as compared with the adhesive core sequence of fibronectin, Arg—Gly—Asp—Ser, (SEQ ID NO.16) and is stable in blood.

Another object of the present invention is to provide a composition for inhibiting metastasis of tumor comprising such a peptide derivative.

To achieve the above objects, we have systematically investigated various sequences of the adhesive core sequence, particularly analogues having other various amino acid residues instead of Gly and Ser residue of the adhesive core sequence Arg—Gly—Asp—Ser (SEQ ID NO.16) and determined the biological activities thereof to find novel peptide derivatives exhibiting sufficient tumor metastasis inhibiting property, stable in bloodstream for long period of time, easily synthesized and not exhibiting any serious side-effect, and finally achieved the present invention.

According to an aspect of the present invention, there is provided a peptide derivative containing 1 to 20 units of a peptide unit represented by the following general formula [I] or a salt thereof;

[Z]—Arg—X—Asp—[Y]　　　[I]

wherein Arg represents L- or D-arginine residue, Asp represents L-aspartic acid residue, X represents L- or D-leucine, D-isoleucine, L- or D-norleucine, L- or D-phenylalanine, D-phenylglycine or D-alanine residue, and [Z] and [Y] each represents an amino acid or a peptide residue, which may be present or absent, selected from glycine, L-serine, L-threonine, L- and D-aspartic acid, L-alanine, L- and D-glutamic acid, L-proline residues and a peptide residue constituted by the foregoing amino acid residues.

According to another aspect of the invention, there is provided a composition for inhibiting tumor metastasis comprising, as an effective ingredient, the peptide derivatives defined above.

DETAILED DESCRIPTION OF THE PREFERRED EMBODIMENTS

The present invention will hereinafter be explained in more detail.

The peptide derivatives of the present invention are those containing 1 to 20 units of the peptide unit represented by the following general formula [I] or a salt thereof;

[Z]—Arg—X—Asp—[Y]     [I]

wherein Arg represents L- or D-arginine residue, Asp represents L-aspartic acid residue, X represents L- or D-leucine, D-isoleucine, L- or D-norleucine, L- or D-phenylalanine, D-phenylglycine or D-alanine residue, and [Z] and [Y] each represents an amino acid or a peptide residue, which may be present or absent, selected from glycine, L-serine, L-threonine, L- and D-aspartic acid, L-alanine, L- and D-glutamic acid, L-proline residues and a peptide residue constituted by the foregoing amino acid residues.

The peptide derivatives of the present invention may be a peptide composed of one unit of the peptide sequence represented by the formula [I], but preferably they are either those composed of oligopeptide or polypeptide comprising two or more of the above peptide units represented by the general formula [I] or those composed of a compound consisting of one or more of the peptide unit represented by the general formula [I] and one or more of pharmaceutically acceptable organic groups bonded to the units, which maintain the water-solubility of the compound and do not reduce the biological activity of the compound.

When the peptide derivatives of the present invention consist of oligopeptide or polypeptide, the carboxyl terminal of the peptides may be amidated.

It has been known that stability of phermaceutical drugs in living bodies after the administration thereof, such as represented by the period of staying in the bloodstream and the period before the drugs are excreted from the living bodies, would greatly influence on whether the drugs may be maintained at a therapeutically effective concentration in the living bodies. That is, not only the biological activity but also the stability of the drugs in living bodies are very important for the drugs to be sufficiently effective. This may be also applied to the peptide sequence of the present invention represented by the formula [I]. If the peptide sequences of the formula [I] are administered by themselves, the peptide sequences may be rapidly degraded and excreted and such rapid degradation and excretion are generally inherent to peptide compounds. Thus, it is not necessarily possible to expect sufficient biological activity of the peptide sequences of the formula [I] when the sequences are administered by themselves. This is the reason why we have investigated various peptide derivatives containing the peptide sequence of the formula [I], such as those composed of oligopeptide containing the sequence as a repeating unit, those containing the sequences bonded to other organic groups and those containing D-amino acids instead of the corresponding L-amino acids, and we finally achieved the present invention.

As explained above, the important purposes of the modification of the peptide sequence with the organic groups are to protect the effective sequence from the degradation by the enzymes in body fluid by modifying the neighborhood of the sequence, to obviate or aim at accumulation of the derivatives in a specific organ by modifying the sequence with acidic groups or saccharide groups, to endow the derivatives with the slow release property by making the sequence contained in high molecular weight compounds, and the like. Therefore, as far as the organic groups to be bonded to the sequence are pharmaceutically acceptable, able to maintain the water-solubility of the compound and do not deteriorate the biological activity of the sequence, various organic groups may be used depending on the purposes.

The organic groups preferably selected from substituted and unsubstituted acyl, alkyl, alkylamino groups, which groups preferably have 1 to 15 carbon atoms and may contain —O—, —NH—, —S—, ester bond, amide bond, urethane bond or urea bond, and groups derived from monosaccharides, oligosaccharides, preferably containing 2 to 7 monosaccharide units, polysaccharaide derivatives, polycarboxylic acids, preferably having 2 to 12 carboxyl groups, polyamines, preferably having 2 to 12 amino groups, polymers formed from monomers having an ethylenically unsaturated bond such as acrylic acid, methacrylic acid, ethacrylic acid and allylamine, polyethylene glycol, preferably having an average molecular weight of 2,000 to 10,000 and carboxylic acid derivative of polyethylene oxide (PEO Acid).

When the organic groups are selected from those derived from the saccharides, the peptide derivatives of the invention preferably contains one to ten units of the peptide sequence of the formula [I]. When the organic groups are selected from those derived from the polycarboxylic acids or polyamines, the peptide derivatives of the invention preferably contains one to five units of the peptide sequence of the formula [I].

The constituent saccharides of the monosaccharides, oligosaccharides and polysaccharides are preferably selected from glucose, galactose, N-acetylglucosamine, glucosamine, N-acetylgalactosamine, gatactosamine, uronic acid, sialic acid and the like, and these saccharides may be used in any combination.

Examples of the polysaccharide include chitin, chitosan, carboxymethylated chitin, sulfated carboxymethylated chitin, chondroitin sulfate, curdlan sulfate, heparin sulfate, keratin sulfate and hyaluronic acid. The polysaccharides preferably have a molecular weight of from 10,000 to 30,000. Those organic groups may have anionic groups such as —SO$_3$ (X), —OSO$_3$ (X), —OPO$_3$ (X), and —CO$_2$ (X), wherein X represents a hydrogen atom or pharmaceutically acceptable counter anion, preferably represents an alkali metal anion.

The peptide sequence and the organic groups are bonded with an ester bond, amide bond, urethane bond, urea bond and the like. In particular, when the organic groups are selected form those derived from monosaccharides, origosaccharides, polysaccharides, polymers and the like, the peptide sequence of the formula [I] and the organic group may be bonded through an alkylene group or an arylene group. In such cases, the alkyl group and arylene group are preferably linear and substituted, preferably have 1 to 15 carbon atoms and may contain —O—, —NH—, —S—, ester bond, amide bond, urethane bond or urea bond.

The organic groups are preferably bonded to the peptide sequence of the formula [I] at the carbocyl terminal or the amino terminal of the peptide sequence. When the organic group is bonded to the peptide sequence at the amino terminal of the peptide sequence, the carboxyl terminal of the peptide sequence is preferably in the form of $-OR_a$ or $-NR_bR_c$, wherein each of $R_a$, $R_b$ and $R_c$ represents a hydrogen atom or a linear or cyclic alkyl group and $R_b$ and $R_c$ may be bonded together to form a ring structure. Further, $R_a$, $R_b$ and $R_c$ may contain $-O-$, $-NH-$, $-S-$, ester bond, amide bond, urethane bond or urea bond. $R_a$, $R_b$ and $R_c$ are preferably selected from methyl, ethy, iso-propyl and cyclohexyl group.

When the organic group is bonded to the peptide sequence at the carboxyl terminal of the peptide sequence, the amino terminal preferably has a hydrogen atom or substituted or unsubstituted acyl group. The acyl group preferably has 1 to 15 carbon atoms. Preferred examples of the substituent of the acyl group are the foregoing anionic groups such as carboxyl group and sulfonic group. The acyl group may contain $-O-$, $-NH-$, $-S-$, ester bond, amide bond, urethane bond or urea bond.

The molecular weight of the peptide derivatives of the present invention is not particularly limited as far as the biological activity of the derivatives is maintained and the whole derivative is maintained as water-soluble, but the average molecular weight thereof preferably ranges from 1,000 to 100,000.

As the salts of the peptide derivatives of the present invention, there may preferably be mentioned, salts with inorganic acids, for instance, hydrochlorides, sulfates, nitrates, phosphates and borates, and salts with organic acid, for instance, acetates, trifluoroacetates, trifluoromethanesulfonates, lactates and tartrates. Conversion of the derivatives into these salts may be carried out by a conventional manner.

Preferred examples of the peptide derivative according to the present invention including those described in Examples (Synthesis of the derivatives and investigation of the biological activities thereof) will be listed below, but the present invention is by no means limited to these specific examples. When the amino terminal of the peptide sequence has a hydrogen atom and when the carboxyl terminal of the peptide sequence has $-OH$, indications of the hydrogen atom and the $-OH$ group are omitted in the formulae in accordance with the orthography in this field. Further, D-amino acids are shown with the indications of "D-", but the indications of "L-" of L-amino acids are omitted.

Compound 1 (SEQ ID NO. 1)
Arg—Leu—Asp—Ser

Compound 2
Arg—D—Leu—Asp—Ser

Compound 3 (SEQ ID NO. 2)
Arg—Nle—Asp—Ser

Compound 4
Arg—D—Nle—Asp—Ser

Compound 5
Arg—D—Phg—Asp—Ser

Compound 6 (SEQ ID NO. 3)
Arg—Phe—Asp—Ser

Compound 7
Arg—D—Phe—Asp—Ser

Compound 8
D—Arg—Leu—Asp—Ser

Compound 9 (SEQ ID NO. 1)
Arg—Leu—Asp—Ser—$NH_2$

Compound 10
Arg—D—Ala—Asp—Thr—$NH_2$

Compound 11
Arg—D—Leu—Asp—Ser—$NHCH_3$

Compound 12
Arg—D—Leu—Asp—Ser—$NH$—$isoC_3H_7$

Compound 13 (SEQ ID NO. 1)
Arg—Leu—Asp—Ser—$NH$—$cycloC_6H_{11}$

Compound 14
D—Arg—Leu—Asp—Ser—Pro—$NHCH_3$

Compound 15 (SEQ ID NO. 4)
Gly—Arg—Leu—Asp—Ser

Compound 16 (SEQ ID NO. 5)
Asp—Arg—Leu—Asp—Ser

Compound 17 (SEQ ID NO. 1)
Arg—Leu—Asp—Ser—$OCH_3$

Compound 18 (SEQ ID NO. 6)
Glu—Arg—Leu—Asp—Ser

Compound 19 (SEQ ID NO. 1)
Succinyl—Arg—Leu—Asp—Ser—NH$_2$

Compound 20 (SEQ ID NO. 1)
Succinyl—Arg—Leu—Asp—Ser

Compound 21
Succinyl—Arg—D—Nle—Asp—Ser

Compound 22
Succinyl—Arg—D—Phe—Asp—Ser

Compound 23
Acetyl—D—Arg—Leu—Asp—Ser

Compound 24 (SEQ ID NO. 2)
Succinyl—Arg—Nle—Asp—Ser

Compound 25
Succinyl—D—Arg—Leu—Asp—Ser

Compound 26 (SEQ ID NO. 5)
C$_4$H$_9$CO—D—Asp—Arg—Leu—Asp—Ser

Compound 27 (SEQ ID NO. 7)
Acetyl—Asp—Arg—Phe—Asp—Ser

Compound 28
Acetyl—D—Asp—Arg—Phe—Asp—Ser

Compound 29
Acetyl—Glu—Arg—D—Leu—Asp—Ser

Compound 30
Acetyl—Asp—Arg—D—Phe—Asp—Ser

Compound 31 (SEQ ID NO. 6)
Acetyl—Glu—Arg—Leu—Asp—Ser—NHC$_3$H$_7$

Compound 32
Acetyl—Asp—D—Arg—Leu—Asp—Ser

Compound 33
Acetyl—D—Asp—Arg—Leu—Asp—Ser—NHCH$_3$

Compound 34 (SEQ ID NO. 1)
C$_4$H$_9$CO—Arg—Leu—Asp—Ser

Compound 35
Acetyl—D—Asp—Arg—Leu—Asp—Ser

Compound 36 (SEQ ID NO. 8)
(Arg—Leu—Asp—Ser)$_4$

Compound 37
(Arg—D—Leu—Asp—Ser)$_4$

Compound 38
(Arg—D—Leu—Asp—Ser)$_3$—NH—isoC$_3$H$_7$

Compound 39
Succinyl—(Arg—D—Leu—Asp—Ser)$_2$—NHCH$_3$

Compound 40
Succinyl—(D—Arg—Leu—Asp—Ser)$_4$

Compound 41
(Gly—Arg—D—Leu—Asp—Ser)$_{10}$

Compound 42
Acetyl—(Asp—Arg—D—Leu—Asp—Ser)$_6$

Compound 43
Acetyl—(Asp—D—Arg—Leu—Asp—Ser)$_{10}$

Compound 44
(Arg—D—Leu—Asp)$_{20}$

Compound 45
(D—Arg—Phe—Asp)$_{20}$

-continued

Compound 46
(Arg—D—Phe—Asp—Ser)$_3$—NH—cycloC$_6$H$_{11}$

Compound 47 (SEQ ID NO. 1)
NaO$_3$S—CH$_2$—CH(CH$_3$)—CO—NHCH$_2$CH$_2$CO—Arg—Leu—Asp—Ser Compound 48
NaO$_3$S—CH$_2$CH$_2$—CO—NHCH$_2$CH$_2$CH$_2$CO—Gly—Arg—D—Ile—Asp—Ser—NHCH$_3$ Compound 49 (SEQ ID NO. 4)
NaO$_3$SCH$_2$CH(CH$_3$)CONHCH$_2$CH$_2$CO—Gly—Arg—L—Leu—Asp—Ser—NH—isoC$_3$H$_7$ Compound 50 (SEQ ID NO. 1)
NaO$_3$SO(CH$_2$)$_3$—CO—Arg—L—Leu—Asp—Ser Compound 51
NaO$_3$SO(CH$_2$)$_{11}$—CO—Gly—D—Arg—L—Phe—Asp—Ser—NH—CH$_3$ Compound 52
H$_3$CCH(OSO$_3$Na)CH$_2$CH$_2$CO—Asp—Arg—D—Leu—Asp—Ser—NH$_2$ Compound 53 (SEQ ID NO. 3)
NaO$_3$SO—CH$_2$CH(OSO$_3$Na)—CO—Arg—Phe—Asp—Ser Compound 54 (SEQ ID NO. 9)
H$_3$CCH(OPO$_3$H$_2$)CH$_2$CH$_2$—CO—Gly—Arg—L—Nle—Asp—Ser Compound 55
NaO$_3$SOCH$_2$CHCONHCH$_2$CH$_2$CO—(Arg—D—Leu—Asp—Ser)$_2$ Compounds 56 to 63 are those polymers formed from each of the following Monomers 56 to 63.

Monomer 56 (SEQ ID NO. 1)
CH$_2$=CCH$_3$—CONHCH$_2$CH$_2$—CO—Arg—Leu—Asp—Ser

Monomer 57 (SEQ ID NO. 1)
CH$_2$=CCH$_3$—CO—Gly—Gly—Arg—Leu—Asp—Ser—NH—CH$_3$

Monomer 58 (SEQ ID NO. 2)
CH$_2$=CCH$_3$—CONHCH$_2$CH$_2$—CO—Arg—Nle—Asp—Ser

Monomer 59
CH$_2$=CH—CONHCH$_2$CH$_2$—CO—Asp—Arg—D—Leu—Asp—Ser

Monomer 60 (SEQ ID NO. 10)
CH$_2$=CCH$_3$—CONHCH$_2$CH$_2$—CO—Gly—Arg—Phe—Asp—Ser—NH—isoC$_3$H$_7$ Monomer 61
CH$_2$=CCH$_3$—CONHCH$_2$CH$_2$CH$_2$CH$_2$—CO—Gly—D—Arg—Leu—Asp—Ser Monomer 62
CH$_2$=CCH$_3$—CO—NHCH$_2$CH$_2$CH$_2$—CO—Arg—D—Phe—Asp—Ser Monomer 63
CH$_2$=CCH$_3$—CO—NHCH$_2$CH$_2$—CO—(Asp—Arg—D—Leu—Ser)$_2$ Compound 64 (SEQ ID NO. 10)
HOOC—C(CH$_2$—O—COCH$_2$CH$_2$—CO—Gly—Arg—Phe—Asp—Ser)$_3$ Compound 65 (SEQ ID NO. 1)
HO$_3$SO—(CH$_2$)$_3$—CO—Arg—Leu—Asp—Ser Compound 66 (SEQ ID NO. 10)
NaO$_3$SO—(CH$_2$)$_{11}$—CO—Gly—Arg—Phe—Asp—Ser—NHCH$_3$ Compound 67
H$_3$C—CH(OSO$_3$Na)—CH$_2$CH$_2$—CO—Asp—Arg—D—Leu—Asp—Ser—NH$_2$ Compound 68
NaO$_3$SO—CH$_2$CH(OSO$_3$Na)—CO—Arg—D—Phe—Asp—Ser Compound 69 (SEQ ID NO. 9)
H$_3$C—CH(OPO$_3$H$_2$)—CH$_2$CH$_2$—CO—Gly—Arg—Nle—Asp—Ser Compound 70 (SEQ ID NO. 1)
NaO$_3$S—CH$_2$CH(CH$_3$)—CONH—CH$_2$CH$_2$—CO—Arg—Leu—Asp—Ser Compound 71
NaO$_3$S—CH$_2$CH$_2$—CONH—CH$_2$CH$_2$CH$_2$—CO—Gly—Arg—D—Ile—Asp—Ser—NHCH$_3$ -continued
Compound 72 (SEQ ID NO. 4)
NaO₃S—CH₂CH(CH₃)—CONH—CH₂CH₂—CO—Gly—Arg—Leu—Asp—Ser—NHCH(CH₃)₂
Compound 73 (SEQ ID NO. 1)
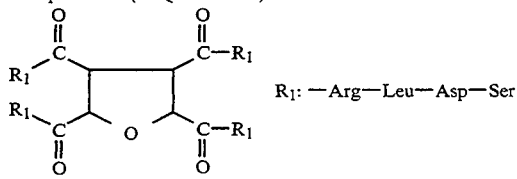   R₁: —Arg—Leu—Asp—Ser
Compound 74 (SEQ ID NO. 1)
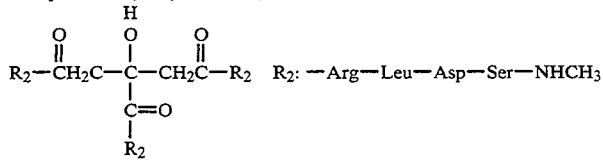   R₂: —Arg—Leu—Asp—Ser—NHCH₃
Compound 75 (SEQ ID NO. 11)
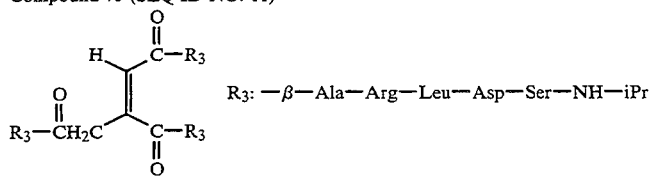   R₃: —β—Ala—Arg—Leu—Asp—Ser—NH—iPr
Compound 76 (SEQ ID NO. 11)
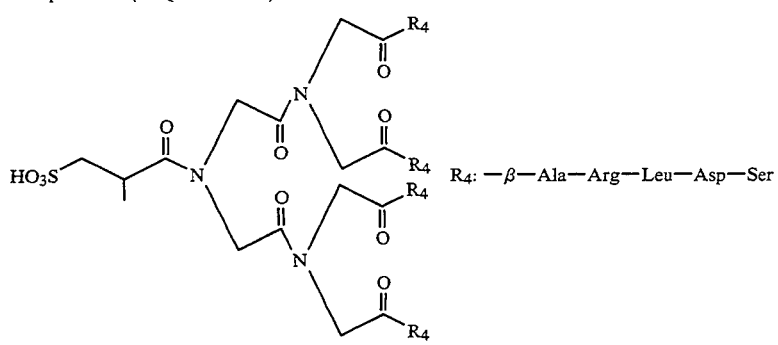   R₄: —β—Ala—Arg—Leu—Asp—Ser
Compound 77 (SEQ ID NO. 11)
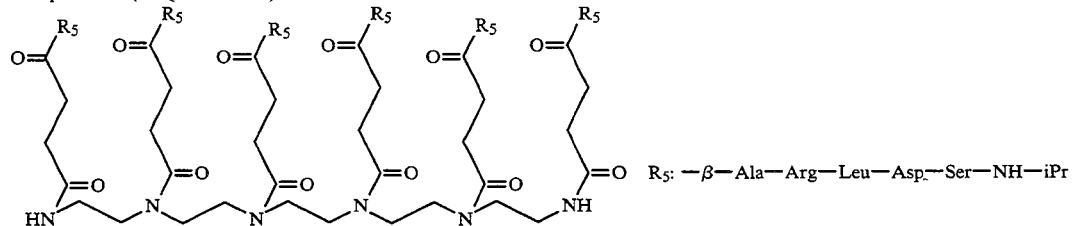   R₅: —β—Ala—Arg—Leu—Asp—Ser—NH—iPr
Compound 78
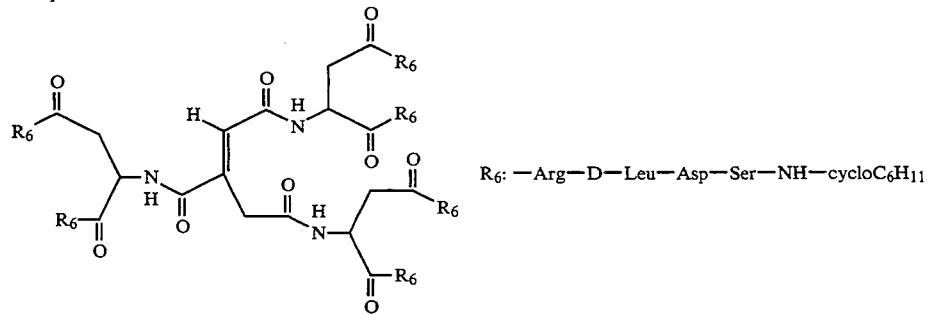   R₆: —Arg—D—Leu—Asp—Ser—NH—cycloC₆H₁₁
Compound 79

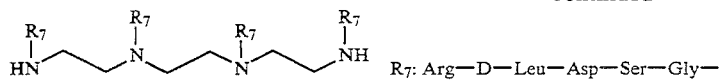
R7: Arg—D—Leu—Asp—Ser—Gly—
Compound 80 (SEQ ID NO. 1)
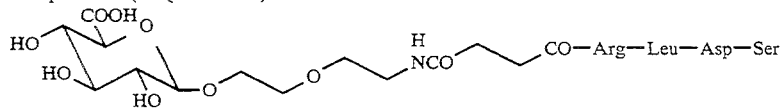
Compound 81 (SEQ ID NO. 12)
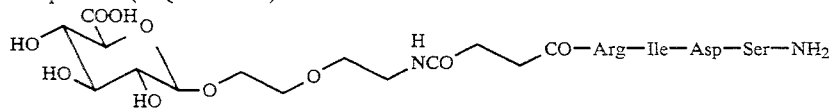
Compound 82
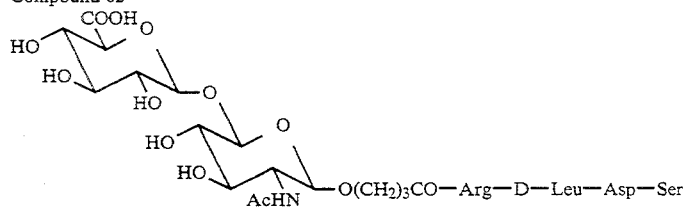
Compound 83 (SEQ ID NO. 3)
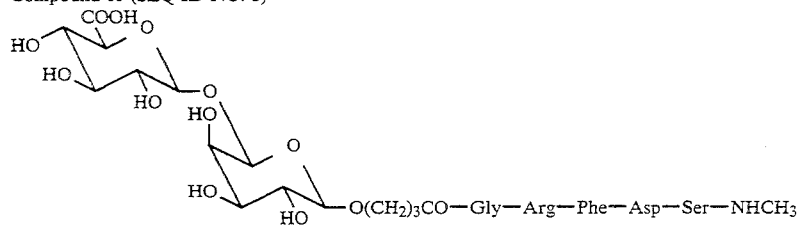
Compound 84
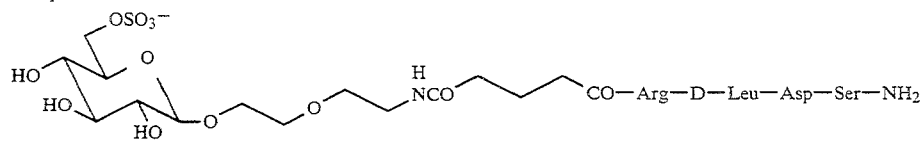
Compound 85
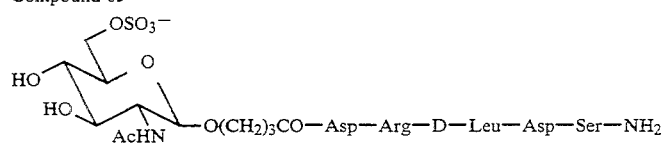
Compound 86 (SEQ ID NO. 4)
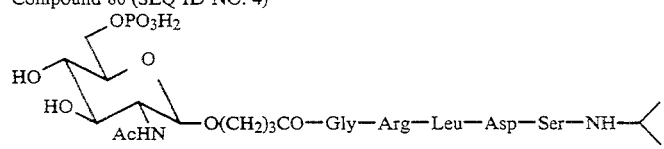
Compound 87
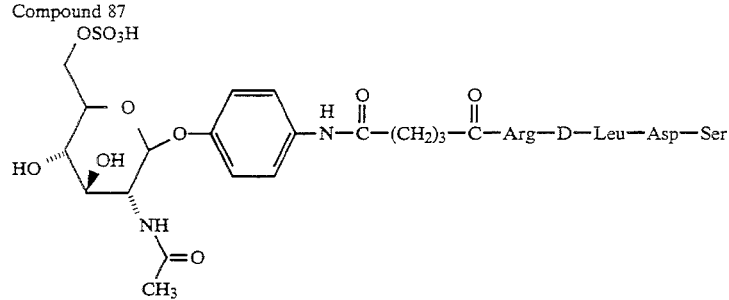

-continued
Compound 88
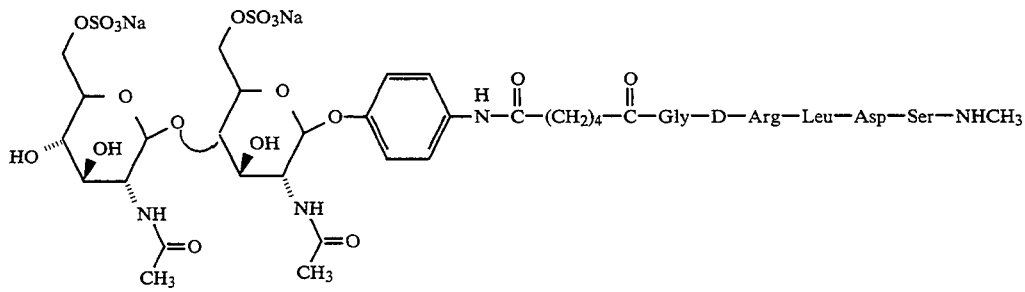
Compound 89 (SEQ ID NO. 10)
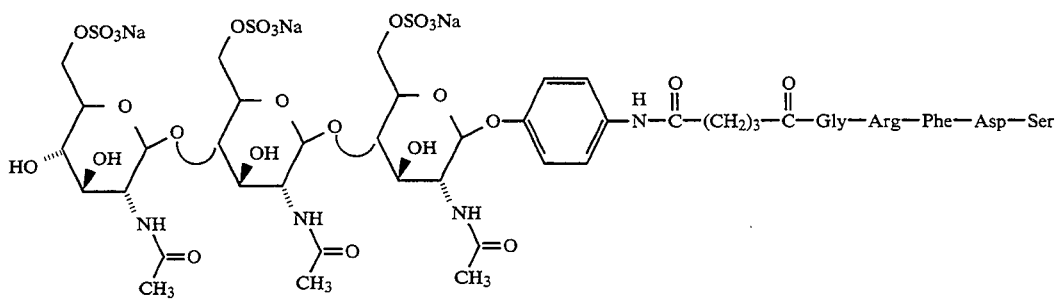
Compound 90
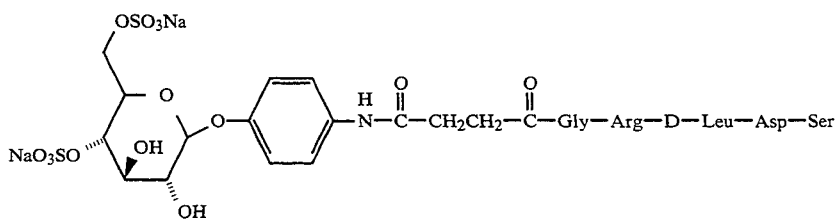
Compound 91
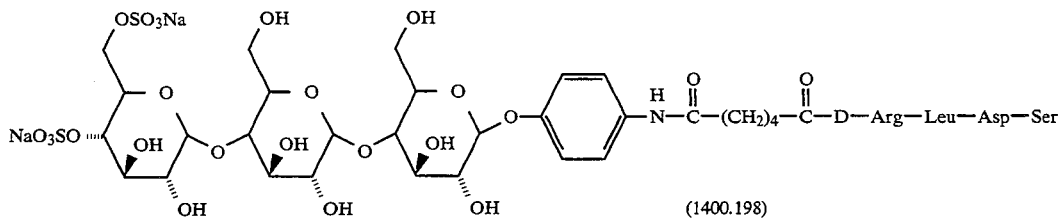
(1400.198)
Compound 92
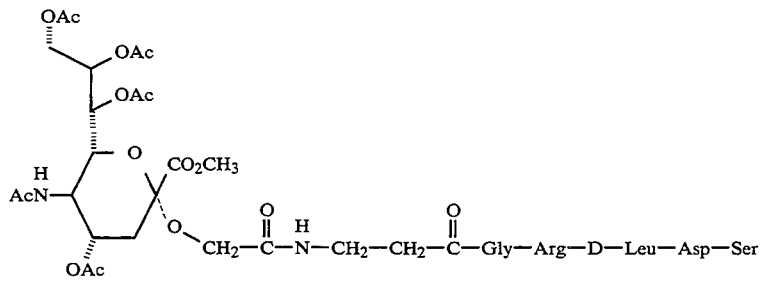
Compound 93

-continued

[Structure: sialic acid derivative with OH, AcNH, CO₂H groups connected via —OCH₂—C(=O)—NH—(CH₂)₃—C(=O)—D-Arg—Leu—Asp—Ser—NHCH₃]

Compounds 94 to 97

[Chitin trisaccharide structure with CH₂OCH₂CO—W substituents, NHCOCH₃ groups]

Compound 94 (SEQ ID NO. 13) W = Asp—Arg—Leu—Asp—Ser    n = 4
Compound 95                  W = Asp—Arg—D—Leu—Asp—Ser   n = 3
Compound 96 (SEQ ID NO. 10) W = Gly—Arg—Phe—Asp—Ser     n = 4
Compound 97                  W = Asp—Arg—D—Phe—Asp—Ser   n = 2

Compounds 98 to 101

[Chitin trisaccharide structure with CH₂O—W₁ substituents, NHCOCH₃ groups]

Compound 98 (SEQ ID NO. 13) W₁ = SO₃H or CH₂CO—Asp—Arg—Leu—Asp—Ser     n = 1-10
Compound 99                  W₁ = SO₃H or CH₂CO—Asp—Arg—D—Leu—Asp—Ser   n = 1-10
Compound 100 (SEQ ID NO. 10) W₁ = SO₃H or CH₂CO—Gly—Arg—Phe—Asp—Ser     n = 1-10
Compound 101                 W₁ = SO₃H or CH₂CO—Asp—Arg—D—Phe—Asp—Ser   n = 1-10

Compound 102
Succinylated polyallylamine carrying    —Arg—D—Leu—Asp—Ser

Compound 103
Succinylated polyallylamine carrying    —(Asp—D—Arg—Phe—Asp—Ser)₂

Compound 104
Arg—D—Leu—Asp—Ser—Gly—    carrying polyallylamine

Compound 105 (SEQ ID NO. 1)
CM-chitin carrying    —Arg—Leu—Asp—Ser

Compound 106
Succinylated CM-chitin carrying    —Gly—Arg—D—Leu—Asp—Ser

Compound 107
Maleyl derivative of CM-chitin carrying    —Asp—Arg—D—Ile—Asp—Ser—NHCH₃

Compound 108
Phthaloyl derivative of CM-chitin carrying    —Asp—D—Arg—Nle—Asp—Ser Compound 109 (SEQ ID NO. 1)
Itaconyl derivative of CM-chitin carrying    —Arg—Leu—Asp—Ser Compound 110
CM-chitin carrying    —Gly—Arg—D—Phe—Asp—Ser—Pro Compound 111
CM-chitin carrying    —Gly—Asp—D—Phg—Asp—Thr—NH₂

Compound 112
Succinylated CM-chitin carrying    —(Arg—D—Leu—Asp—Ser)₂

Compound 113 (SEQ ID NO. 9)

-continued

Sulfated CM-chitin carrying —Gly—Arg—Nle—Asp—Ser—NH—CH₃

Compound 114
Sulfated CM-chitin carrying —Gly—D—Arg—Leu—Asp—Ser

Compound 115 (SEQ ID NO. 3)
Sulfated Succinylated CM-chitin carrying —Arg—Phe—Asp—Ser—NH—iso—C₃H₇

Compound 116
Sulfated Succinylated CM-chitin carrying —Arg—D—Leu—Asp—Ser—Pro—NHC₂H₅

Compound 117
Chondroitin sulfate carrying —Gly—D—Arg—Leu—Asp—Ser—NH—isoC₃H₇

Compound 118
Succinylated chondroitin sulfate carrying —D—Arg—Phe—Asp—Ser

Compound 119
Maleyl derivative of chondroitin sulfate carrying —Arg—D—Leu—Asp—Ser Compound 120
Trimellityl derivative of chondroitin sulfate carrying —Glu—Arg—Phg—Asp—Ser Compound 121
Succinylated chondroitin sulfate carrying —(Arg—D—Leu—Asp—Ser)₂

Compound 122
Succinylated chondroitin sulfate carrying —(Arg—D—Leu—Asp—Ser)₅

Compound 123 (SEQ ID NO. 14)
Cyanurate PEG₁ (Arg—Leu—Asp—Ser)₂

Compound 124
Cyanyrate PEG₂ —Arg—D—Leu—Asp—Ser

Compound 125 (SEQ ID NO. 4)
R₈OCCH₂(OCH₂CH₂)ₙOCH₂COR₈  R₈: —Gly—Arg—Leu—Asp—Ser, $\overline{M}$: 4,900

Compound 126 (SEQ ID NO. 15)
R₉OCCH₂(OCH₂CH₂)ₙOCH₂COR₉  R₉: —Gly—Arg—Leu—Asp—Ser—Pro—NH₂, $\overline{M}$: 5,200

Compound 127 (SEQ ID NO. 1)

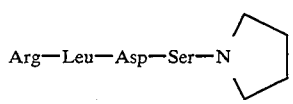

Compound 128

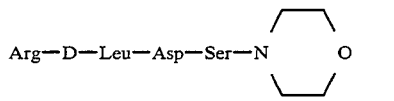

Compound 129

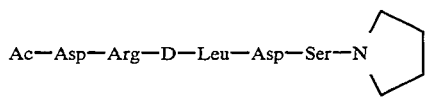

Methods for synthesizing the peptide sequences are not particularly limited to any specific method and a suitable method may be selected from liquid phase methods, solid phase methods and methods utilizing an automatic synthesizer depending on the kind of the organic group to be bonded with the peptide sequences. In the solid phase methods, oligopeptides are synthesized using Boc groups, cleavage of the peptides from a resin carrier and elimination of the protection groups on the side chain are carried out using trifluoromethanesulfonic acid and the peptides or the derivatives thereof are purified by HPLC (high performance liquid chromatography) for fractionation and collected as fractions showing a single peak. For example, the peptide derivatives of the present invention, Compounds 36, 37 and 40 to 46 may be fractionated by using a YMC-Pack ODS column (length: 500 mm, inner diameter: 20 mm) and a suitable eluent such as 0.01N HCl/acetonitrile, 0.1% TFA/acetonitrile and 0.1% TFA/water. The eluent may have a suitable gradient. The peptides are then converted into hydrochloric acid salt, acetic acid salt or the like by passing through an anion-exchange resin column such as Amberlite IRA-400; Cl form and IRA-93ZU; acetic acid salt form. Though thus obtained peptide may be directly reacted with the organic groups, they may be modified with the organic groups before the cleavage from the resin carrier. In the synthesis by the liquid phase methods, the peptides are generally synthesized in the properly protected form, optionally deprotected at a specific modification site or sites and modified, and then totally deprotected.

Though only the representative examples of the synthesis of the protected peptides are described herein, the details of the synthesis methods of protected peptides are described in, for example, Lectures on Biochemical Experiments, "Chemistry of Proteins IV", p 207 to 495, edited by the Biochemical Society of Japan, published by Tokyo Kagaku Dojin; Lectures on Biochemical Experiments, Second Series, "Chemistry of Proteins (the last volume)", edited by the Biochemical Society of Japan, published by Tokyo Kagaku Dojin and "Fundamental Knowledge and Experiments of Peptide Synthesis", edited by Izumiya et al., published by Maruzen. Alternatively, it is also possible to use commercially available synthetic peptides as intermediates. The peptides composed of repeating units may be easily synthesized by the continuous polymerization method by means of diphenylphosphoryl azide (DPPA) by N. Nishi et al., Int. J. Peptide Protein Res., 30, p 275 (1987). In addition, the peptides may be prepared by the methods of genetic engineering.

Synthesis of the saccharide moiety may be carried out by using glycosylation reaction as a key reaction. Various methods of the glycosylation are known and the reaction conditions may be selected taking account of the kinds and availability of saccharides and the conditions of the deprotection. The synthesis of saccharide is carried out essentially by condensation reaction of a sugar donor and a sugar receptor of alcohol in the presence of a promoter. For example, when sugar chloride, sugar bromide and the like are used as the sugar donor, silver oxide, silver carbonate, silver perchlorate, silver trifluoromethanesulfonate, mercury (II) cyanide, mercury bromide and the like may be used as the promoter. When sugar fluoride and the like are used as the sugar donor, tin (II) chloride/silver perchlorate, zirconocene dichloride/silver perchlorate and the like may be used as the promoter. When alkylthio compounds of sugar are used as the sugar donor, dimethyl(methylthio)sulfonium triflate, methyl trifluoromethane sulfonate ester, phenylselenyltriflate and the like may be used as the promoter. When imidate compounds are used as the sugar donor, the reaction is carried out by using lewis acids such as boron trifluoride/diethyl ether complex. Dehydration desiccating agents such as molecular sieves and Drylite may be used in the glycosylation reactions explained above. When the sugar donor has a reducing terminal sugar of 2-acetoamido-2-deoxy sugar such as N-acetylglucosamine, the glycosylation reaction may be effectively carried out by the oxazoline method.

Sugar residues of aryl glycoside may be synthesized by using a reaction of polyacetylated sugar and phenol which are heated in nonpolar solvent such as benzene and toluene as the key step. Further, as regards p-nitrophenyl glycoside compounds, many of such compounds are commercially available.

S-glycosides may be synthesized by the Koenig-Knorr method wherein the sugar donors of sugar chloride, sugar bromide and the like are reacted with thiol compounds. Nucleophilic reactivity of thiol compounds is higher than that of alcohols, and therefore the reaction easily proceeds.

When the peptide sequences and the pharmaceutically acceptable organic groups are bonded with amide bonds or ester bonds, the peptide derivatives of the present invention may be prepared by the active ester methods, the mixed acid anhydride method, the azide method, the acid chloride method, the symmetric acid anhydride method, the DCC method, the DCC-additive method, the carbonyldiimidazole method and the like.

The peptide derivatives composed of polymers such as propeneamide derivatives may prepared by conventional radical polymerization method, ion polymerization method and the like. Resulted polymers may be fractionated depending on the molecular weight thereof by conventional methods such as gel filtration, dialysis and the like.

The mechanism of the potent in vivo activity for inhibiting tumor metastasis of the peptide derivatives or the salts thereof according to the present invention is not completely elucidated. However, it was clearly shown that the cell-migration (infiltration) inhibitory activity in an in vitro system of the present peptide derivatives is superior to that of the peptide Arg—Gly—Asp—Ser, which is the minimum unit of the cell-adhesive proteins for exhibiting the adhesive function, though the cell-adhesion inhibitory activity and the platelet-coagulation inhibitory activity in an in vitro system of the present peptide derivatives are not necessarily superior to those of Arg—Gly—Asp—Ser. Therefore, the peptide derivatives or the salts thereof according to the present invention can be administered to patients optionally together with conventional carriers or pharmaceutical auxiliary agents, i.e., as a composition containing at least one of the peptide derivatives of the present invention, as tumor or cancer metastasis inhibiting agents. The administration dose thereof may vary depending on conditions of disease to be treated, age and body weight of patients and the like, but generally ranges from $0.2 \mu$ g/kg to 400 mg/kg a day.

The peptide derivatives of the present invention may be administered through various routes which are generally used for the administration of peptide-containing medicines. For example, it is preferably administered parenterally, e.g., intravenously, intramuscularly and subcutaneously. In the preparation of injectable pharmaceutical preparations containing the peptide derivatives of the present invention, the derivatives are dissolved in, for example, PBS and physiological saline solution as described hereinbelow, or dissolved in about 0.1N aqueous solution of acetic acid and then lyophilized to give a lyophilized preparation. These pharmaceutical preparations may comprise a conventional stabilizer such as glycine and albumin. In addition, the peptide derivative of the present invention may orally administered in the form of microcapsule by encapsulating the derivatives in, for example, liposomes and microspheres or in the form of hydrogel. Further, if the derivatives are formulated in the form of, for example, suppository, sublingual tablets and nasal sprays, they can be absorbed through mucous other than digestive tracts.

The present invention will hereinafter be explained in more detail with reference to the following non-limitative examples but the present invention is by no means limited to these specific Examples.

The abbreviations used herein are listed below. In the descriptions hereinbelow, D-amino acid residues are described with the indications of "D-" but as regards L-amino acid residues, the indications of "L-" are omitted.

Boc: t-butoxycarbonyl
Bn: benzyl
Z: benzyloxycarbonyl
Ac: acetyl

Su: succinyl
Me: methyl
Et: ethyl
iPr: isopropyl
OSu: N-hydroxysuccinimide
ONb: nitrobenzyl ester
Mts: mesitylenesulfonyl
HOBt: 1-hydroxybenzotriazole
DCC: dicyclohexylcarbodiimide
iPr2NEt: diisopropylethylamine
AcOH: acetic acid
AcOEt: ethyl acetate
DMF: dimethylformamide
CDI: carbonyldiimidazole
TFA: trifluoroacetic acid
DC-urea: dicyclohexylurea
Thr: threonine
Arg: arginine
Gly: glycine
Asp: aspartic acid
Ser: serine
Pro: proline
Val: valine
Leu: leucine
Phe: phenylalanine
Phg: phenylglycine
Ile: isoleucine
Nle: norleucine
Glu: glutamic acid
Ala: alanine

EXAMPLE 1

Synthesis of Compound 1

Compound 1 was synthesized by following Route 1 below.

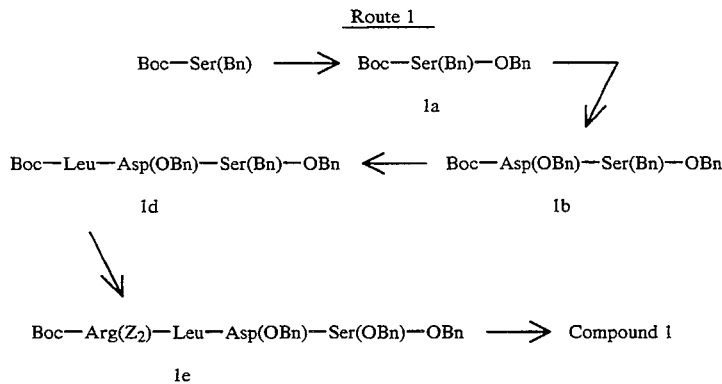

Synthesis of Compound (1a)

To a DMF solution (150 ml) containing t—Boc—Ser(Bn) (14.8 g, 50 mmol) and NaHCO$_3$ (8.4 g, 0.1 mol), benzyl bromide (8.55 g, 50 mmol) was added dropwise, and the solution was stirred for 24 hours at room temperature. The reaction solution was extracted by adding 4% aqueous solution of Na$_2$CO$_3$ and ethyl acetate and the organic and aqueous layers were separated. The ethyl acetate layer was washed with water and saline solution successively and dried over sodium sulfate. The organic solvent was evaporated under reduced pressure to give 17.0 g (4.4 mol) of Compound (1a) as an oily product. Yield: 88%.

Synthesis of Compound (1b)

Compound (1a) (17.0 g, 44 mmol) was dissolved in methylene chloride (30 ml), added with TFA (30 ml) and dried over 3 hours at room temperature. After removing methylene chloride and TFA by means of a rotatory evaporator, the residue was extracted by adding ethyl acetate and 4% aqueous solution of Na$_2$CO$_3$ and the organic layer was separated. The organic layer was washed with water and saline solution successively and dried over sodium sulfate. After evaporating the solvent under reduced pressure, the residue was dissolved in a mixed solvent of methylene chloride (60 ml) and DMF (40 ml), added with t—Boc—Asp(OBn) (15 g, 46 mmol) and HOBt monohydrate (HOBt.H$_2$O, 6.7 g, 44 mmol) and stirred with ice cooling. The reaction mixture was added with DCC (10.3 g) and stirred for 2 hours with ice cooling and overnight at room temperature. Then, the precipitated urea derivative was removed by filtration and the filtrate was concentrated under reduced pressure. The residue was extracted by adding ethyl acetate and 4% aqueous solution of Na$_2$CO$_3$ and the organic layer was separated. The ethyl acetate layer was washed with water and saline solution successively and dried over sodium sulfate. After removing newly precipitated urea derivative by filtration, the filtrate was concentrated under reduced pressure. The residue was purified by silica gel column chromatography (n-hexane/ethyl acetate=2/1) to give Compound (1b) (15.8 g, 26.7 mmol) as a white solid. Yield: 61%. Synthesis of Compound (1c)

Compound (1c) (15.5 g, 26.2 mmol) was dissolved in methylene chloride (30 ml), added with TFA (30 ml) and stirred for 30 minutes at room temperature. After removing ethylene chloride and TFA by means of a rotary evaporator, the residue was added with a mixed solvent of n-hexane and ether (5:1) and precipitated white solid of Compound (1c) (15.0 g, 24.8 mmol) was taken by filtration. Yield: 95%.

Synthesis of Compound (1d)

A reaction mixture containing Compound (1c) (1.5 g, 2.48 mmol), t—Boc—Leu.H$_2$O (690 mg, 2.96 mmol), HOBt.H$_2$O (380 mg, 2.5 mmol) and diisopropyl ether (0.470μ 1, 2.7 mmol) in methylene chloride (15 ml) and DMF (7 ml) was stirred with ice cooling.

This reaction mixture was added with DCC (570 mg) and stirred for 2 hours with ice cooling and overnight at room temperature. After removing precipitated urea derivative by filtration, the filtrate was concentrated under reduced pressure. The residue was added with ethyl acetate and washed with 10% aqueous solution of citric acid, 4% aqueous solution of Na$_2$CO$_3$, water and saline solution successively. After removing newly precipitated urea derivative by filtration, the filtrate was concentrated under reduced pressure. The residue was purified by silica gel column chromatography (n-hexane/ethyl acetate=10/1) to give Compound (1d) (1.39 g, 2 mmol) as a white solid. Yield: 80%.

Synthesis of Compound (1e)

Compound (1d) (1.15 g, 1.6 mmol) was dissolved in methylene chloride (6 ml), added with TFA (6 ml) and stirred for 1 hour at room temperature. After evaporating methylene chloride and TFA by means of a rotatory evaporator, the residue was extracted by adding ethyl acetate and 4% aqueous solution of Na$_2$CO$_3$ and the organic layer was separated. The ethyl acetate layer was washed with water and saline solution successively and dried over sodium sulfate. After evaporating the ethyl acetate under reduced pressure, the residue was dissolved in a mixed solvent of methylene chloride (15 ml) and DMF (8 ml), added with t—Boc—Arg(Z$_2$) (970 mg, 1.8 mmol) and HOBt.H$_2$O (220 mg, 1.4 mmol) and stirred with ice cooling. The reaction mixture was added with DCC (420 mg) and stirred for 2 hours with ice cooling and overnight at room temperature. Then, the precipitated urea derivative was removed by filtration and the filtrate was concentrated under reduced pressure. The residue was extracted by adding ethyl acetate and 4% aqueous solution of Na$_2$CO$_3$ and the organic layer was separated. The ethyl acetate layer was washed with water and saline solution successively and dried over sodium sulfate. After removing newly precipitated urea derivative by filtration, the filtrate was concentrated under reduced pressure. The residue was purified by silica gel column chromatography (chloroform/ethyl acetate=10/1) and recrystallized from a mixed solvent of n-hexane and ethyl acetate (2/1) to give Compound (1e) (690 mg, 0.61 mmol) as a white solid. Yield: 38%, M.P.: 100°-104° C.

Synthesis of Compound 1

Compound (1e) (590 mg, 0.53 mmol) was dissolved in methylene chloride (6 ml), added with TFA (6 ml) and stirred for 30 minutes at room temperature. After removing ethylene chloride and ethyl acetate by means of a rotatory evaporator, the residue was added with acetic acid (10 ml) and 10% palladium/carbon (Pd/C, 60 mg) and hydrogenolysis was carried out overnight at room temperature. After removing the catalyst by filtration and evaporating acetic acid under reduced pressure, the residue was added with ether and precipitate was taken by filtration.

Thus obtained crude peptide was dissolved in a small amount of water (pH 1-2) and developed in a column of Amberlite IRA93ZU (acetic acid form) with pure water. Positive fractions in the ninhydrin reaction (pH 4-5) were combined, concentrated and finally lyophilized to give Compound 1 (240 mg) as a white amorphous product. In the proton NMR, a peak of methyl group of acetic acid was observed at 2.02 ppm, of which integral intensity showed that Compound 1 was obtained as a monosalt of acetic acid. Yield: 82%.

FAB Mass: 490 (M+H)$^+$

EXAMPLE 2

Synthesis of Compound 8

Condensation reaction was carried out in the same manner as in the synthesis of Compound (1e) by using t—Boc—D—Arg(Z$_2$) in stead of t—Boc—Arg(Z$_2$) to obtain Compound 8 in the totally protected form. Yield: 40%, M.P.: 136°-139° C.

Hydrogenolysis and purification of the totally protected Compound 8 (620 mg, 0.55 mmol) were carried out in the same manner as in the synthesis of Compound 1 to obtain Compound 8 as a monosalt of acetic acid (280 mg). Yield: 84%.

FAB Mass: 490 (M+H)$^+$

EXAMPLE 3

Synthesis of Compound 23

The fully protected Compound 8 (4.02 g, 3.56 mmol) was dissolved in methylene chloride (30 ml), added with TFA (30 ml) and stirred for 1 hour at room temperature. After removing methylene chloride and TFA by means of a rotatory evaporator, the residue was extracted by adding chloroform and 4% aqueous solution of Na$_2$CO$_3$ and the organic was separated. The organic layer was washed with water and saline solution successively and dried over sodium sulfate. By evaporating chloroform under reduced pressure, Compound (1e) of which t—Boc was eliminated (3.56 g, 3.46 mmol) was obtained. Yield: 97%.

Thus obtained t—Boc-eliminated Compound (1e) (1.36 g, 1.32 mmol) was dissolved in methylene chloride (15 ml), added with acetic anhydride (0.15 ml) and stirred for 2 hours at room temperature. Formed precipitate was taken by filtration and recrystallized from acetonitrile to give Compound 23 in the totally protected form (930 mg, 0.87 mmol). Yield 66%, M.P.: 163°-166° C.

The totally protected product (930 mg) was dissolved in acetic acid (15 ml) and 10% palladium/carbon (90 mg) and hydrogenolysis was carried out for 1 hour at 40° C. and overnight at room temperature. After removing the catalyst by filtration and evaporating acetic acid under reduced pressure, the residue was added with ether and resulted precipitate was taken by filtration.

Thus obtained crude peptide was dissolved in pure water, added with activated carbon and stirred for 15 minutes at room temperature. After removing the activated carbon by filtration and evaporating water, the residue was lyophilized to give Compound 23 (290 mg). Yield 61%.

FAB Mass: 532 (M+H)$^+$, 554 (M+Na)$^+$

EXAMPLE 4

Synthesis of Compound 20 t—Boc-eliminated Compound (1e) (1.1 g, 1.07 mmol) obtained in the same manner as in Example 3 was dissolved in methylene chloride (15 ml), added with succinic anhydride (130 mg) and stirred for 2 hours at room temperature. After evaporating the solvent under reduced pressure, the residue was recrystallized from acetonitrile to give Compound 20 in the totally protected form (1.18 g, 1.05 mmol). Yield 98%, M.P.: 167°-169° C.

The totally protected product (1.0 g, 0.886 mmol) was dissolved in acetic acid (15 ml) and 10% palladium/carbon (90 mg) and hydrogenolysis was carried out for 1 hour at 40° C. and overnight at room temperature. After removing the catalyst by filtration and evaporating acetic acid under reduced pressure, the residue was added with ether and resulted precipitate was taken by filtration.

Thus obtained crude peptide was dissolved in pure water, added with activated carbon and stirred for 15 minutes at room temperature. After removing the activated carbon by filtration and evaporating water, the residue was lyophilized to give Compound 20 (480 mg). Yield 92%.

FAB Mass: 590 (M+H)+

EXAMPLE 5

Synthesis of Compound 17

A methylene chloride solution (60 ml) containing t—Boc—Ser(Bn) (8.86 g, 30 mmol), N,N-dimethylaminopyridine (360 mg) and methanol (1.4 ml) was stirred with ice cooling and added with DCC (6.2 g). After stirring the solution overnight, methylene chloride was evaporated and the residue was added with ethyl acetate (40 ml). After removing formed urea derivative by filtration, the ethyl acetate filtrate was washed with an aqueous solution of citric acid, aqueous solution of $NaHCO_3$ and saline solution successively and dried over magnesium sulfate. After evaporating ethyl acetate under reduced pressure, crude t—Boc—Ser(Bn)—$OCH_3$ (9.3 g) was obtained as a colorless oily product.

Compounds (17b) to (17e) were prepared by following the above described Route 1 and using the above obtained crude t—Boc—Ser(Bn)—$OCH_3$ instead of Compound (1a). Compounds (17b) to (17e) have a methyl ester group at the serine residue instead of the benzyl ester group of Compounds (1b) to (1e).

Yields of the preparation steps are as follows.
(17b) 79%,
(17c) 86%,
(17d) 75%,
(17e) 62%, M.P. 130°–132° C.

Compound 17 was prepared as a monosalt of acetic acid in the same manner as in Example 4 by using Compound (17e) instead of Compound (1e).

FAB Mass: 604 (M+H)+

EXAMPLE 6

Amidation of Carboxyl Terminal

The amidation at the carboxyl terminal of the peptide according to the invention may be carried out by either of the active esterification method and the DCC method. A typical example of the conversion into an amide compound is given below. Synthesis of Boc—Ser(Bn)—NHMe Boc—Ser(Bn)—OH (29.5 g, 0.1 mol) and p-nitrophenol (13.9 g, 0.1 mol) were dissolved in a mixed solvent of methylene chloride (20 ml) and DMF (20 ml) and added with DCC (20.6 g, 0.1 mol) with ice cooling. The reaction mixture was stirred for 1 hour with ice cooling and overnight while allowing the mixture to warm up to room temperature. The mixture was filtered through a Celite layer to remove the precipitate, and the Celite layer was washed with ethyl acetate. The filtrate and the washing liquor were combined and concentrated under reduced pressure to obtain crude p-nitrophenyl ester compound. This product was dissolved in THF (150 ml) and added with 40% methylamine solution. The reaction mixture was stirred for 20 hours at room temperature and concentrated under reduced pressure. The residue was purified by silica gel chromatography (eluent: hexane/ethyl acetate=2/1) to obtain the desired methylamide compound as colorless powder (29.6 g). Yield 96%.

Other amide compounds may be obtained in a similar manner.

EXAMPLE 7

Synthesis of Compound 16

Compound (1e) (4.2 g, 3.7 mmol) was dissolved in methylene chloride (20 ml), added with TFA (20 ml) and stirred for 1 hour at room temperature. After removing the methylene chloride and the TFA by means of a rotatory evaporator, the residue was extracted by adding chloroform and 4% aqueous solution of $Na_2CO_3$ and the organic was separated. The chloroform layer was washed with water and saline solution successively and dried over sodium sulfate. After evaporating the chloroform under reduced pressure, the residue was dissolved in a mixed solvent of methylene chloride (30 ml) and DMF (30 ml), added with t—Boc—Asp (OBn) (1.3 g, 45 mmol) and $HOBt.H_2O$ (610 mg, 4.0 mmol) and stirred with ice cooling. The reaction mixture was added with DCC (850 mg) and stirred for 2 hours with ice cooling and overnight at room temperature. After removing precipitated urea derivative by filtration, the filtrate was concentrated under reduced pressure. The residue was extracted by adding chloroform and 4% $Na_2C_3$ aqueous solution and the organic layer was separated. The ethyl acetate layer was washed with water and saline solution successively, and newly precipitated urea derivative was removed by filtration. The filtrate was concentrated under reduced pressure and dried over magnesium sulfate. After evaporating the ethyl acetate under reduced pressure, the residue was recrystallized from a mixed solvent of ethyl acetate and n-hexane (3:1) and then from acetonitrile to give t—Boc—Asp(OBn)—Arg($Z_2$)—Leu—Asp(OBn)—Ser(Bn)—OBn (3.2 g, 2.4 mmol) as a colorless solid product. Yield: 65%.

Compound 16 was prepared through t—Boc eliminating reaction, acetylation reaction, hydrogenolysis and purification similar to those of Example 4 by using above-obtained totally protected product instead of Compound (1e).

FAB Mass: 647 (M+H)+, 669 (M+Na)+

EXAMPLE 8

Synthesis of Compound 18

In the same manner as used in the synthesis of Compound 16, Compound 18 was prepared by using t—Boc—Glu(OBn) instead of t—Boc—Asp(OBn).

FAB Mass: 661 (M+H)+

EXAMPLE 9

Synthesis of Compounds 2 to 7

Compounds (2d), (3d), (4d), (5d), (6d) and (7d) were prepared in the same manner as used in the synthesis of the intermediate compound for the synthesis of Compound 1, Compound (1d), by using t—Boc—D—Leu, t—Boc—Nle, t—Boc—D—Nle, t—Boc—D—Phg, t—Boc—Phe and t—Boc—D—Phe instead of t—Boc—Leu respectively. Then, Compounds (2e), (3e), (4e), (5e), (6e) and (7e) were prepared in the same manner as used in the synthesis of Compound (1e) by using Compounds (2d), (3d), (4d), (5d), (6d) and (7d)

respectively instead of Compound (1d). Finally, deprotection and purification of Compounds (2e), (3e), (4e), (5e), (6e) and (7e) were carried out in the same manner as used in Example 1 to obtain Compounds 2 to 7 in the form of monosalt of acetic acid.

Yields of the reactions, melting points and mass spectrum data of the above-obtained compounds according to the present invention are listed below.

TABLE 1

| Yield (%) | | |
|---|---|---|
| Compound (2d) 87 | Compound (2e) 76 | Compound 2 88 |
| Compound (3d) 86 | Compound (3e) 84 | Compound 3 87 |
| Compound (4d) 69 | Compound (4e) 69 | Compound 4 86 |
| Compound (5d) 86 | Compound (5e) 81 | Compound 5 92 |
| Compound (6d) 91 | Compound (6e) 65 | Compound 6 82 |
| Compound (7d) 66 | Compound (7e) 78 | Compound 7 80 |

TABLE 2

| Melting point (°C.) | |
|---|---|
| Compound (2e) | 126–127 |
| Compound (3e) | 139–141 |
| Compound (4e) | 131–134 |
| Compound (5e) | 147–151 |
| Compound (6e) | 124–127 |
| Compound (7e) | 141 |

TABLE 3

| FAB Mass | |
|---|---|
| Compound 2 | 490 (M + H)$^+$, 512 (M + Na)$^+$ |
| Compound 3 | 490 (M + H)$^+$ |
| Compound 4 | 490 (M + H)$^+$ |
| Compound 5 | 510 (M + H)$^+$ |
| Compound 6 | 524 (M + H)$^+$, 546 (M + Na)$^+$ |
| Compound 7 | 524 (M + H)$^+$, 546 (M + Na)$^+$ |

EXAMPLE 10

Synthesis of Compound 56

(a) An aqueous solution of sodium hydroxide containing β-alanine (17.8g, 0.2 mol) was added with methacryloyl chloride (20.9 g, 0.2 mol) with ice cooling, stirred for 4 hours and neutralized with hydrochloric acid. After concentrating the reaction mixture under reduced pressure, precipitated sodium chloride was removed by filtration. The concentrate was extracted with chloroform and dried. After evaporating the chloroform, the concentrate was washed with ether to obtain carboxymethylmethacrylamide as a white solid product (17.6 g). Yield: 56%.

CH$_2$=CCH$_3$—CONHCH$_2$CH$_2$—COOH

In the same manner as described above, various-propenoic acid derivatives may be prepared, for example, from combinations of methacryloyl chloride and 4-aminobutyric acid, ethacryloyl chloride and 5-aminovaleric acid, methacrylic acid and 6-aminocaproic acid, acrylic acid and 12-aminolauric acid, acrylic acid and leucine, methacrylic acid and glutamine, acrylic acid and 2-(2-aminoethoxy)propyonic acid, methacrylic acid and 2-(2aminoethoxy)acetic acid, methacrylic acid and glycylglycine and the like.

(b) Synthesis of Boc—Arg(Mts)—Leu—Asp(OBn)—Ser(Bn)—OBn

Boc—Lue—Asp(OBn)—Ser(Bn)—OBn (Compound (1d)) (28 g, 39 mmol) was added with a mixed solvent (200 ml) of TFA and CH$_2$Cl$_2$ (1:1) and stirred for 1 hour at room temperature, and then the TFA and CH$_2$Cl$_2$ were evaporated under reduced pressure. The residue was dissolved in ethyl acetate, neutralized with NaHCO$_3$ aqueous solution and washed with NaCl aqueous solution. The mixture was dried over sodium sulfate, and the ethyl acetate was evaporated under reduced pressure.

Thus obtained product and Boc—Arg(Mts) (17.8 g, 39 mmol) were dissolved in DMF (400 ml), added with DCC (8.0 g, 39 mmol) and HOBt (6.8 g, 45 mmol) with ice cooling and stirred for 3 hours with ice cooling and overnight at room temperature. After removing DC-urea by filtration, the reaction mixture was concentrated under reduced pressure and the residue was dissolved in ethyl acetate. This solution was washed with NaHOC$_3$ aqueous solution, 1M citric acid aqueous solution and NaCl aqueous solution successively, dried over sodium sulfate and evaporated to dryness under reduced pressure to obtain the desired compound as white powder (19.5 g). Yield: 48%.

(c) Synthesis of Monomer 56

Boc—Arg(Mts)—Leu—Asp(OBn)—Ser(Bn)—OBn (15.6 g, 15 mmol) was added with a mixed solvent (100 ml) of TFA and CH$_2$Cl$_2$ (1:1) and stirred for 1 hour at room temperature, and then the solvent was evaporated under reduced pressure. The residue was dissolved in ethyl acetate, neutralized with NaHCO$_3$ aqueous solution and washed with NaCl aqueous solution. The mixture was dried over sodium sulfate, and the ethyl acetate was evaporated under reduced pressure.

Thus obtained product and carboxyethylmethacrylamide (2.4 g, 15 mmol) were dissolved in CH$_2$Cl$_2$ (200 ml), added with DCC (3.1 g, 15 mmol) and stirred for 3 hours with ice cooling and further stirred overnight at room temperature. The reaction mixture was concentrated under reduced pressure and added with acetone, and formed DC-urea was removed by filtration. The mixture was concentrated under reduced pressure, washed with ether and dried under reduced pressure to obtain white powder (10.0 g). Yield: 62%.

The above obtained product (10.0 g, 9.3 mmol) was dissolved in TFA, added with a solution of 1M-trifluoromethanesulfonic acid/thioanisole/m-cresol in TFA with ice cooling and allowed to react for 1 hour to eliminate the protection groups present on the side chain and the terminal of the peptide. The reaction solution was poured into ether, resulted oily precipitate was dissolved in distilled water, then washed with ethyl acetate, passed through an anion-exchange resin column (Amberlite IRA-400; Cl form) to convert into a hydrochloride and lyophilized to give the desired monomer as a white solid product (4.4 g). Yield: 76%.

Amino Acid Analysis (nmol/50 μl)
Arg: 0.9877
Leu: 0.9916
Asp: 0.9899
Ser: 0.8891
β-Ala: 1.0115
Mass Spectra (MS): M$^+$573

(d) Synthesis of Compound 56 (Polymerization of Monomer 56)

Monomer 56 (500 mg) was dissolved in water (5 ml), adjusted the pH value at 7.4 with 1N NaOH and added with potassium persulfate (2.5 mg) and sodium hydrogensulfite (1.0 mg) as initiators and allowed to cause polymerization reaction under nitrogen flow at 20° C. for 20 hours.

After the reaction, the reaction mixture was dialyzed against pure water using Spectrapore 7 (MWCO: 3000) to eliminate low molecular weight compounds and lyophilized to obtain the desired Compound 56 (240 mg).

The obtained Compound 56 was fractionated according to the molecular weight thereof by gel permeation chromatography, which was carried out by using TSK Gel G3000SW column available from Toso Co., Ltd., and 0.2M phosphate buffer (pH 7.4) as a mobile phase at a flow rate of 1.0 ml/min. The determined molecular weight of the fractions of Compound 56 are as follows (Standard: PEG).

Fraction 1 Molecular weight: about 48,000 (Compound 56-1)
Fraction 2 Molecular weight: about 21,000 (Compound 56-2)
Fraction 3 Molecular weight: about 12,000 (Compound 56-3)

EXAMPLE 11

Synthesis of Compound 56-4 (Synthesis of Low Molecular Weight Polymer by Altering the Amount of Initiator)

Compound 56-4 was prepared in the same manner as used in Example 10 by using the following initiators.
Initiator: Potassium persulfate 10 mg
Sodium hydrogensulfite 4 mg
Yield: 180 mg
Molecular weight: about 5,000

EXAMPLE 12

Synthesis of Reference Polymer A

The above-synthesized carboxyethylmethacrylamide was polymerized through radical polymerization reaction as follows. Carboxyethylmethacrylamide (2 g) was dissolved in DMF (20 ml), added with a radical initiator V65 (2,2-azobis(2,4-dimethylvaleronitrile, Wako Junyaku Co., Ltd., 10 mg) and allowed to cause polymerization under nitrogen flow at 65° C. for hours. The resulted polymer was precipitated with ethyl acetate, dialyzed against pure water using Spectrapore (MWCO: 3000) to eliminate low molecular weight fraction and lyophilized to obtained Reference Polymer A (1.24 g).

Reference Polymer A
H—($CH_2$—$CHCH_3$ ($CONHCH_2CH_2COOH$))$_n$
Molecular weight (Standard: PEG): about 30,000

EXAMPLE 13

Synthesis of Monomer 57

Monomer 57 was prepared in the same manner as used in Example 10 by using the following reagents and the amounts thereof.
(a) Synthesis of Boc—Asp(OBn)—Ser(Bn)—NHCH$_3$
Boc—Asp(OBn): 32.3 g (0.1 mol)
Ser(Bn)NHCH$_3$ HCl: 24.4 g (0.1 mol)
N-methylmorpholine: 10.1 g (0.1 mol)
CH$_2$Cl$_2$: 500 ml
DCC: 20.6 g (0.1 mol)
Yield: 44.2 g (Mw 513.6)
(b) Synthesis of Boc—Leu—Asp(OBn)—Ser(Bn)—NHCH$_3$
Product of (a): 25.6 g (0.05 mol)
TFA/CH$_2$Cl$_2$: 150 ml/150 ml
Boc—Leu: 11.5 g (0.05 mol)
CH$_2$Cl$_2$: 300 ml
DCC: 10.3 g (0.05 mol)
Yield: 20.1 g (Mw 614.7)

(c) Synthesis of Boc—Arg(Mts)—Leu—Asp(OBn)—Ser(Bn)—NHCH3
Product of (b): 20.7 g (0.03 mol)
TFA/CH$_2$Cl$_2$: 100 ml/100 ml
Boc—Arg(Mts): 13.7 g (0.03 mol)
DMF: 250 ml
DCC: 6.18 g (0.03 mol)
HOBt: 4.0 g (0.03 mol)
Yield: 17.5 g (Mw 953.1)
(d) Synthesis of Boc—Gly—Arg(Mts)—Leu—Asp(OBn)—Ser(Bn)—NHCH$_3$
Product of (c): 9.53 g (0.01 mol)
TFA/CH$_2$Cl$_2$: 100 ml/100 ml
Boc—Gly: 1.75 g (0.01 mol)
DMF: 80 ml
DCC: 2.06 g (0.01 mol)
HOBt: 1.36 g (0.01 mol)
Yield: 6.53 g (Mw 1009.9)
(e) Synthesis of Boc—Gly—Gly—Arg(Mts)—Leu—Asp(OBn)—Ser(Bn)—NHCH$_3$
Product of (d): 5.04 g (0.005 mol)
TFA/CH$_2$Cl$_2$: 50 ml/50 ml
BOC—Gly: 0.88 g (0.005 mol)
DMF: 200 ml
DCC: 1.03 g (0.005 mol)
HOBt: 0.68 g (0.005 mol)
Yield: 3.84 g (Mw 1066.7)
(f) Synthesis of Monomer 57
Product of (e): 3.20 g (0.003 mol)
TFA/CH$_2$Cl$_2$: 40 ml/40 ml
Methacrylic acid: 0.22 g (0.003 mol)
DMF: 60 ml
DCC: 0.62 g (0.003 mol)
HOBt: 0.41 g (0.003 mol)
TFA solution of 1M-Trifluoromethanesulfonic acid/thioanisole/m-cresol: 25 ml
(Amberlite IRA-400; Cl form treatment)
Amino Acid Analysis (nmol/50 μl)
Arg: 0.9845
Gly: 2.1361
Asp: 0.9554
Ser: 0.8879
Leu: 0.9472
MS: M+ 656

EXAMPLE 14

Synthesis of Monomer 59

Monomer 59 was prepared in the same manner as used in Example 10.
$CH_2$=$CHCONHCH_2CH_2CO$—Asp—Arg—D—Leu—Asp—Ser
Yield: 35%
Amino Acid Analysis (nmol/50 μl)
Arg: 0.9982
Ser: 1.0319
Asp: 1.9971
D—Leu: 1.0063
β-Ala: 1.024
MS: M+ 729 (729.75)

EXAMPLE 15

Synthesis of Monomer 62

Monomer 62 was prepared in the same manner as used in Example 10.
$CH_2$=$CCH_3CONHCH_2CH_2CH_2CO$—Arg—Phg—Asp—Ser Yield: 24%
Amino Acid Analysis (nmol/50 μl)
Arg: 1.0028
Phg: 1.0014
Asp: 1.0043
Ser: 0.9963
4-aminobutyric acid: 1.0257
MS: M+ 662 (662.67)

EXAMPLE 16

Synthesis of Monomer 61

Monomer 61 was prepared in the same manner as used in Example 10.

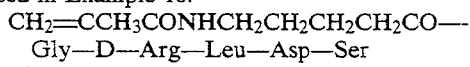
CH$_2$=CCH$_3$CONHCH$_2$CH$_2$CH$_2$CH$_2$CO—Gly—D—Arg—Leu—Asp—Ser

Yield: 17%
Amino Acid Analysis (nmol/50 μl)
D—Arg: 1.0056
Gly: 1.0012
Asp: 0.9645
Leu: 1.0177
Ser: 1.0090
MS: M+ 713, 713.8

EXAMPLE 17

Synthesis of Monomer 63

Monomer 63 was prepared in the same manner as used in Example 10.

CH$_2$=CCH$_3$CONHCH$_2$CH$_2$CO—(Asp—Arg—D—Leu—Ser)$_2$

Yield: 10%
Amino Acid Analysis (nmol/50 μl)
Arg: 2.0484
D—Leu: 2.0965
Asp: 2.0333
Ser: 2.1032
β-Ala: 1.0449
MS: M+ 1100 (1100.21)

EXAMPLE 18

Synthesis of Compounds 57 to 63 (Polymerization of Monomers 57 to 63)

Polymerization of Monomers 57 to 63 was carried out in the same manner as used in Example 10(d).

| Compound No. | Yield (mg) | Molecular weight |
|---|---|---|
| 57 | 230 | 9,500 |
| 58 | 180 | 13,000 |
| 59 | 190 | 9,000 |
| 60 | 190 | 11,000 |
| 61 | 240 | 16,000 |
| 62 | 150 | 11,000 |
| 63 | 170 | 10,000 |

EXAMPLE 19

Synthesis of Succinylated Polyallylamine

Polyallylamine (5.2 g, Nitto Boseki Co., Ltd.) and triethylamine (15.2 g) were dissolved in water (100 ml), added with 4-dimethylaminopyridine (1.7 g) and succinic anhydride (15.0 g) and stirred overnight at room temperature. The desired compound, succinylated polyallylamine, was precipitated with acetone, washed with ether and dried. Yield: 1.26 g, Molecular weight 11,000.

EXAMPLE 20

Synthesis of Compound 102

Succinylated Polyallylamine Carrying
—Arg—D—Leu—Asp—Ser

The succinylated polyallylamine (0.39 g) obtained in Example 19 was dissolved in phosphate buffer (25 ml, pH 7.4), added with a solution of 1-ethyl-3-(dimethylaminopropyl)carbodiimide (0.26 g) in phosphate buffer (5.0 ml ) at 0° C. and allowed to react for 1.5 hours. Then, the reaction solution was added with a solution of Arg—D—Leu—Asp—Ser (0.71 g) dissolved in phosphate buffer (10 ml) and allowed to react overnight at 4° C. The reaction solution was dialyzed against ion-exchanged water and then against pure water using Extrapore 7 (MWCO: 8000) to eliminate low molecular weight compounds, purified and lyophilized. Yield: 0.71 g.

The structure of the product was confirmed by IR and elemental analysis. As a result of the elemental analysis, the introduction rate of the peptide fragment was found to be about 15%. The introduction rate was calculated as described in Example 44.

Elemental Analysis: N; 19.80%
IR: Stretching vibration of amidocarbonyl (C=O) 1648 cm$^{-1}$

EXAMPLE 21

Synthesis of Compound 103

Succinylated Polyallylamine Carrying
—(Asp—D—Arg—Phe—Asp—Ser)$_2$

By using succinylated polyallylamine (0.66 g) obtained in Example 19, (Asp—D—Arg—Phe—Asp—Ser)$_2$ (0.85 g) as the peptide fragment and water-soluble DCC (0.26 g), Compound 103 was prepared in the same manner as used in Example 20. Yield: 0.71 g.

The structure of the product was confirmed by IR and the elemental analysis. As a result of the elemental analysis, the introduction rate of the peptide fragment, (Asp—D—Arg—Phe—Asp)$_2$, was found to be about 9%.

Elemental Analysis: N; 19.44%
IR: Stretching vibration of amidocarbonyl (C=O) 1648 cm$^{-1}$

EXAMPLE 22

Synthesis of Compound 104

Arg—D—Leu—Asp—Ser—Gly— Carrying Polyallylamine

The protected peptide having a free carboxyl group described in Example 31 (6) (4.04 g, 4 mmol) was dissolved in DMF (40 ml), added with DCC (0.83 g, 4 mmol) and HOBt (0.54 g, 4 mmol) with ice cooling and stirred for 1 hour. The reaction mixture was added with polyallylamine hydrochloride (0.78 g) dissolved in DMF (20 ml) and stirred for 3 hours with ice cooling and overnight at room temperature. Then, after removing formed DC-urea, the reaction mixture was concentrated under reduced pressure. Deprotection of the product was carried out in the same manner as used in the synthesis of Monomer 56 (Example 10 (c)). Yield: 0.82 g.

TFA solution of 1M-Trifluoromethansulfonic acid/thioanisole/m-cresol: 150 ml
(Amberlite IRA-400; Cl form treatment)

The structure of the product was confirmed by IR and elemental analysis. As a result of the elemental analysis, the introduction rate of the peptide fragment was found to be about Elemental Analysis: N; 24.93%

IR: Stretching vibration of amidocarbonyl (C=O) 1652 cm$^{-1}$

EXAMPLE 23

Synthesis of Compound 65

Compound 65 was prepared by following Route 2 below.

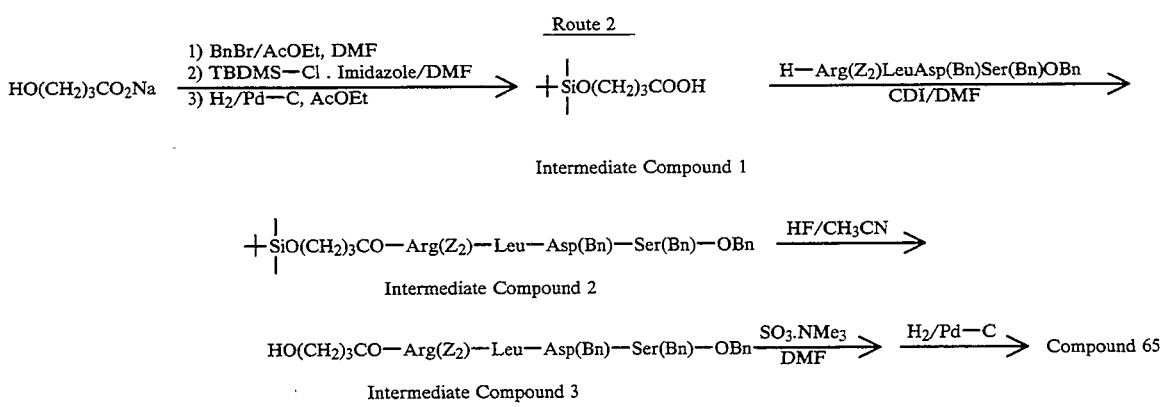

Route 2

Intermediate Compound 1

Intermediate Compound 2

Intermediate Compound 3

(a) Synthesis of Intermediate Compound 1

Sodium 4-hydroxybutyrate (25 g, 0.2 mol) and benzyl bromide (37 g, 0.22 mol) were dissolved in a mixed solvent of DMF (40 ml) and ethyl acetate (50 ml), and the reaction mixture was heated and refluxed for 4 hours. Then, the reaction mixture was allowed to cool to room temperature, diluted with a proper amount of ethyl acetate, washed with saturated saline solution, dried over anhydrous sodium sulfate and concentrated under reduced pressure to give an oily product. The resulted product was purified by silica gel column chromatography (eluent:hexane/ethyl acetate=4/1) to give 34.9 g of benzyl 4-hydroxybutyrate. Yield: 90%.

Thus obtained benzyl 4-hydroxybutyrate (19.4 g, 0.1 mol) and imidazole (10.2 g, 0.15 mol) were dissolved in DMF (100 ml), added with t-butyldimethylsilyl chloride (16 g, 0.11 mol) and stirred overnight at room temperature. After evaporating a major part of the solvent under reduced pressure, the residue was diluted with ethyl acetate, washed with water and saturated saline solution, dried over anhydrous sodium sulfate and concentrated under reduced pressure to give an oily product. The resulted product was purified by silica gel column chromatography (eluent: hexane/ethyl acetate=10/1) to give 29.8 g of benzyl 4-t-butyldimethylsilyloxybutyrate as a colorless oily product. Yield: 97%.

Thus obtained benzyl 4-t-butyldimethylsilyloxybutyrate (29 g, 94 mmol) was dissolved in ethyl acetate (400 ml), added with 10% palladium/carbon (1.5 g) and stirred for 18 hours under hydrogen atmosphere at room temperature. The catalyst was removed by filtration through a Celite layer, and the Celite layer was washed with ethyl acetate. The filtrate and the washing liquor were combined and concentrated under reduced pressure to give 20 g of the objective Intermediate Compound 1 as a colorless oily product. Yield: 98%.

(b) Synthesis of Intermediate Compound 2

Intermediate Compound 1 (440 g, 2 mmol) was dissolved in dry DMF (10 ml) and added with a solution of CDI (330 mg, 2 mmol) in dry DMF (10 ml). The reaction mixture was stirred for 1 hour with ice cooling and added with a solution of H—Arg(Z$_2$)—Leu—Asp(Bn)—Ser(Bn)—OBn (2.06 g, 2 mmol) in DMF (25 ml). The reaction mixture was stirred for 4 hours with ice cooling and overnight while allowing to warm up to room temperature, and the solvent was evaporated under reduced pressure. The residue was diluted with chloroform, washed with water and saturated saline solution, dried over anhydrous sodium sulfate and concentrated under reduced pressure. The residue was crystallized with ether to give 2.13 g of the objective Intermediate Compound 2. Yield: 87%, FAB-MS: (M+H)$^+$ 1228.

(c) Synthesis of Intermediate Compound 3

Intermediate Compound 2 (2.1 g, 1.7 mmol) was dissolved in acetonitrile (30 ml), added with 5 drops of 46% hydrofluoric acid and stirred for 2 hours at room temperature. After confirming the completion of the reaction by TLC, the reaction mixture was poured into a saturated solution of sodium hydrogencarbonate and extracted with chloroform. The combined chloroform layer was washed with water and saturated saline solution, dried over anhydrous sodium sulfate and concentrated under reduced pressure. The residue was crystallized with ether to give 1.8 g of the objective Intermediate Compound 3 as colorless powder. Yield: 95%, FAB-MS: (M+H)$^+$ 1114.

(d) Synthesis of Compound 65

Intermediate Compound 3 (1.8 g, 1.6 mmol) was dissolved in dry DMF (15 ml), added with sulfur trioxide/trimethylamine complex (500 mg, 3.6 mmol) and stirred for 20 hours at room temperature. After confirming the disappearance of the starting compounds, the reaction was stopped by adding a proper amount of saturated aqueous solution of sodium hydrogencarbonate, and the major part of the solvent was evaporated under reduced pressure. The residue was crystallized with ether, and the obtained crystals were washed and dried to obtain a sulfuric acid ester compound. This ester compound was dissolved in acetic acid (20 ml), added with 10% palladium/carbon (100 mg) and stirred for 40 hours under hydrogen atmosphere. The catalyst was removed by filtration through a Celite layer, and the Celite layer was washed with water. The filtrate and washing water were combined and concentrated under reduced pressure. The residue was dissolved in a small amount of water, purified by gel permeation chromatography using Sephadex G-10 and lyophilized to obtain 610 mg of the objective Compound 65 as colorless powder. Yield: 59%, FAB-MS: (M−H)⁻ 654.

EXAMPLE 24

Synthesis of Compound 47

Monomer 56 (620 mg, 1 mmol) was dissolved in water (20 ml), added with sodium hydrogensulfite (300 mg, 3 mmol), and the reaction mixture was heated and stirred for 23 hours at 70° C. After allowing the reaction mixture to cool down to room temperature, a major portion of the water was evaporated under reduced pressure. The residue was dissolved in a small amount of water, purified by gel permeation chromatography using Sephadex G-10 and lyophilized to obtain 580 mg of the objective Compound 47 as colorless powder. Yield: 80%, FAB-MS: (M−H)⁻ 709.

EXAMPLE 25

Synthesis of Compound 73

Tetrahydrofuran-2,3,4,5-Tetracarboxylic Acid (Arg—Leu—Asp—Ser)$_4$

Tetrahydrofurantetracarboxylic acid (0.13 g, 0.5 mmol) was dissolved in DMF (10 ml), added with CDI (0.35 g, 2.2 mmol) with cooling at 0° C. and allowed to react for 2 hours. The reaction mixture was added with trifluoroacetic acid salt of Arg($Z_2$)—Leu—Asp(OBn-)—Ser(Bn)—OBn (2.40 g, 2.1 mmol) and diisopropylethylamine (0.28 g, 2.2 mmol) and allowed to react for 2 hours at 0° C. and for 24 hours at room temperature. After evaporating DMF, the residue was recrystallized from ethyl acetate to obtain 0.60 g (0.14 mmol) of the objective compound in the protected form. The protected compound (0.60 g) was dissolved in acetic acid (10 ml), and hydrogenolysis was carried out in a conventional manner using Pd/C as a catalyst to obtain the objective Compound 73, tetrahydrofuran-2,3,4,5-tetracarboxylic acid (Arg—Leu—Asp—Ser)$_4$ (SEQ ID NO:1)$_4$ (0.28 g, 0.13 mmol)

Amino Acid Analysis (nmol/50 μl)
Arg: 3.7352
Leu: 3.6256
Asp: 3.7157
Ser: 3.2917
MS: M+H⁺ 2133

EXAMPLE 26

Synthesis of Compound 74

Citric acid (Arg—Leu—Asp—Ser—NHCH$_3$)$_3$ (SEQ ID NO:1)$_4$

Citric acid (0.19 g, 1.0 mmol) and trifluoroacetic acid salt of Arg($Z_2$)—Leu—Asp(OBn)—Ser(Bn)—NHCH$_3$ (3.19 g, 3.0 mmol) were dissolved in DMF (40 ml) and added with HOBt (0.40 g), DCC (0.62 g, 3.0 mmol) and diisopropylethylamine (0.39 g, 3.0 mmol) with cooling at 0° C. After 2 hours, the mixture was allowed to warm up to room temperature and to react overnight. After the completion of the reaction, urea was removed and DMF was evaporated. The residue was recrystallized from ethyl acetate to obtain the objective compound in the protected form (0.79 g, 0.26 mmol). Hydrogenolysis of this product was carried out in the same manner as used in Example 73 to obtain the objective citric acid (Arg—Leu—Asp—Ser—NHCH$_3$)$_3$ (SEQ ID NO:1)$_3$ (0.39 g, 0.24 mmol).

Amino Acid Analysis (nmol/50 μl)
Arg: 3.4512
Leu: 3.3499
Asp: 3.4332
Ser: 3.0414
MS: (M+H⁺) 1645

EXAMPLE 27

Synthesis of Compound 75

Aconitic Acid (β-Ala—Arg—Leu—Asp—Ser—NH—iPr)$_3$ (SEQ ID NO:11)$_3$

Trans-aconitic acid (0.17 g, 1.0 mmol) and trifluoroacetic acid salt of β-Ala—Arg(Mts)—Leu—Asp(OBn-)—Ser(Bn)—NH—iPr (SEQ ID NO:11) (3.23 g, 3.0 mmol) were condensed with CDI in DMF. The product was treated as in Example 73 to obtain the objective compound in the protected form (0.67 g, 0.22 mmol). The protected compound was dissolved in trifluoroacetic acid (10 ml), added with a trifuluoroacetic acid solution of 1M-trifluoromethanesulfonic acid/thioanisole/m-cresol with ice cooling at 0° C. and allowed to react for 1 hour to eliminate the protective group on the side chains and at the terminal of the peptide. The reaction mixture was poured into ether, and resulted oily precipitate was dissolved in distilled water, washed with ethyl acetate, passed through an anion-exchange resin column (Amberlite IRA400; Cl form) to convert the product into hydrochloride and lyophilized to obtain the objective aconitic acid (β-Ala—Arg—Leu—Asp—Ser—NH—iPr)$_3$ (SEQ ID NO:11)$_3$ (0.29 g, 0.15 mmol).

Amino Acid Analysis (nmol/50 μ)
β-Ala: 3.1009
Arg: 3.0881
Leu: 2.9975
Asp: 3.0720
Ser: 2.7214
MS: (M+H⁺) 1924

EXAMPLE 28

Synthesis of Compound 76

Iminodiacetic Acid-Tetracraboxylic Acid Derivative (β-Ala—Arg—Leu—Asp—Ser)$_4$ (SEQ ID NO:11)$_4$ Diethyliminodiacetic acid (1.89 g, 0.010 mol) were dissolved in DMF (30 ml) and added with triethylamine (1.5 g, 0.015 mol) and (Boc)$_2$O (2.4 g, 0.011 mol) while stirred with ice cooling. The reaction mixture was stirred for 30 minutes at room temperature, concentrated under reduced pressure, dissolved in ethyl acetate, washed with water and dried. The residue was concentrated and crystallized to obtain Boc-diethyliminodiacetic acid (2.60 g). Yield: 90%.

Boc-dietyliminodiacetic acid (2.60 g) was dissolved in methanol (100 ml), added with 1M NaOH (1.1 eq.) and stirred for 1 hour. After the completion of the reaction, methanol was evaporated and the reaction mixture was added with 10% citric acid and extracted with ethyl acetate. The ethyl acetate layer was washed with water, dried, concentrated and crystallized to give Boc-iminodiacetic acid (1.86 g). Yield: 89%.

Boc-iminodiacetic acid (1.89 g, 0.008 mol) and diethyliminodiacetic acid (3.0 g, 0.016 mol) were condensed with CDI (2.60 g, 0.016 mol) in DMF. After evaporating DMF, the residue was dissolved in ethyl acetate, washed with an aqueous solution of NaHCO$_3$ and water, dried, concentrated and recrystallized from ethyl acetate/hexane. The resultant was again saponified to give the objective tetracarboxylic acid (2.85 g). Yield: 77%.

The obtained tetracarboxylic acid (0.23 g, 0.5 mmol) and trifluoroacetic acid salt of β-Ala—Arg(Mts)—Leu—Asp(OBn)—Ser(Bn)—OBn (SEQ ID NO:11) (2.25 g, 2.0 mmol) were condensed with CDI (0.32 g, 2.0 mmol) in DMF. After evaporating DMF, the residue was crystallized from ethyl acetate to obtain a protective compound (0.67 g, 0.15 mmol).

The protected compound (0.67 g) was treated with TFA to eliminate the Boc group, dissolved in DMAc (20 ml) and added with triethylamine (40 mg). The mixture was further added with a solution of methacryloyl chloride (21 mg) in DMAc (2 ml) and allowed to react for 1 hour. The reaction mixture was poured into water, and resulted precipitates were recovered, washed with water and then with ether and recrystalized from ethyl acetate to give a methacrylamide derivative (0.53 g, 0.12 mmol). Deprotection of this methacrylamide derivative (0.53 g) was carried out in the same manner as used in Example 75 to obtain methacrylamide of iminodiacetic acid-tetracraboxylic acid derivative (β-Ala—Arg—Leu—Asp—Ser)$_4$ (SEQ ID NO:11)$_4$ (0.29 g, 0.11 mmol). This methacrylamide derivative was treated with sodium hydrogensulfite in the same manner as used in Example 24 to obtain the objective compound quantitively (0.29 g, 0.11 mol).

Amino Acid Analysis (nmol/50 µl)
β-Ala: 3.6405
Arg: 3.7707
leu: 3.7271
Asp: 3.8197
Ser: 3.3838
MS: (M+H+) 2682

EXAMPLE 29

Synthesis of Compound 77

Succinylated Pantaethylenehexaamine
(β-Ala—Arg—Leu—Asp—Ser—NH—iPr)$_6$ (SEQ ID NO:11)$_6$ Pentaethylenehexaamine (3.56 g, 0.015 mol) was dissolved in ethanol (80 ml), added with succinic anhydride (20.0 g, 0.20 mol) and a solution of triethylamine (20.0 g) in methanol (20 ml) and allowed to react overnight. After the completion of the reaction, methanol and triethylamine were evaporated under reduced pressure, and the residue was dissolved in water and treated with a cation-exchange resin (Amberlite IRA-120B (H+)). The eluate was lyophilized to obtain succinylated pantaethylenehexaamine (1.04 g, 0.004 mol).

Succinylated pantaethylenehexaamine (0.23 g, 1.0 mmol) and trifluoroacetic acid salt of β-Ala—Arg(Mts)—Leu—Asp(OBn)—Ser(Bn)—NH—iPr (SEQ ID NO:11) (6.45 g, 6.0 mmol) were condensed with CDI in DMF, and the resulted product was treated as in Example 73 to obtain the objective compound in the protected form (1.17 g, 0.18 mmol). Deprotection of the protected compound was carried out in the same manner as used in Example 75 to obtain the objective succinylated pantaethylenehexaamine (β-Ala—Arg—Leu—Asp—Ser—NH—iPr)$_6$ (SEQ ID NO:11)$_6$ (0.54 g, 0.13 mmol)

Amino Acid Analysis (nmol/50 µl)
β-Ala: 4.8209
Arg: 4.6912
Leu: 4.5448
Asp: 4.4577
Ser: 4.1263
MS: (M+H+) 4163

EXAMPLE 30

Synthesis of Compound 78

Aconitic Acid Triaspartylamide
(Arg—D—Leu—Asp—Ser—NH—cycloC$_6$H$_{11}$)$_6$

Trans-aconitic acid (1.83 g, 0.0105 mol) and Asp-(OBn)$_2$ (13.5 g) were dissolved in DMF (40 ml), added with DCC (6.60 g, 0.032 mol) and HOBt (4.32 g, 0.032 mol) at 0° C., allowed to react for 2 hours, warmed up to room temperature and allowed to react overnight at room temperature. After removing urea and evaporating DMF under reduced pressure, the residue was crystallized from ethanol/hexane, washed with ether and dried under reduced pressure to give aconitic acid triaspartylamide (8.71 g, 8.2 mmol). This product was dissolved in acetic acid (40 ml) and subjected to hydrogenolysis using palladium/carbon catalyst to obtain hexacarboxylic acid (3.89 g, 7.5 mmol). The hexacarboxylic acid (0.52 g, 1.0 mmol) and trifluoroacetic acid salt of Arg(Mts)—Leu—Asp(OBn)—Ser(Bn)—NH—cycloC$_6$H$_{11}$ (6.26 g, 6.0 mmol) were condensed with CDI in DMF, and the product was treated as in Example 73 to obtain the objective compound in the protected form (0.91 g, 0.15 mmol). Deprotection of this protected compound was carried out in the same manner as used in Example 75 to obtain the objective Aconitic acid triaspartylamide (Arg—D—Leu—Asp—Ser—NH—cycloC$_6$H$_{11}$)$_6$ (0.46 g, 0.12 mmol).

Amino Acid Analysis (nmol/50 µl)
Arg: 5.2567
Leu: 5.1025
Asp: 5.2293
Ser: 4.6328
MS: (M+H+) 3832

EXAMPLE 31

Synthesis of Compound 79

(Arg—D—Leu—Asp—Ser—Gly)$_4$
Triethylenetetramide

1. Synthesis of peptide fragment

Boc—Arg(Mst)—D—Leu—Asp(OBn)—Ser(Bn)—Gly

The above protected peptide was synthesized in a liquid phase by a sequential-extension method.

(1) Synthesis of Boc—Gly—ONb

Boc—Gly (35 g, 0.2 mol), triethylamine (28 ml, 0.2 mol) and p-nitrobenzyl bromide (43.2 g, 0.2 mol) were dissolved in ethyl acetate (400 ml), refluxed for 5 hours and left overnight at room temperature. The resulted salt was taken by filtration, washed with an aqueous solution of NaHCO$_3$ and water, dried over sodium sulfate, concentrated under reduced pressure and recrystallized from ethyl acetate/hexane to obtain the objective compound (52.7 g, 0.17 mol).

(2) Synthesis of Boc—Ser(Bn)—Gly—ONb

Boc—Gly—ONb (46.5 g, 0.15 ml) was added with TFA/CH$_2$Cl$_2$ (1: 1, 400 ml) and stirred for 1 hour at room temperature. After evaporating TFA/CH$_2$Cl$_2$ under reduced pressure, the residue was dissolved in ethyl acetate, neutralized with an aqueous solution of NaHCO$_3$, washed with an aqueous solution of NaCl and dried over sodium sulfate. Then the ethyl acetate was evaporated under reduced pressure.

This product and Boc—Ser(Bn) (41.7 g, 0.15 mol) were dissolved in CH$_2$Cl$_2$ (750 ml), added with DCC (30.9 g, 0.15 mol), stirred with ice cooling for 3 hours and further stirred at room temperature. After evaporating CH$_2$Cl$_2$ under reduced pressure, the residue was dissolved in ethyl acetate, washed with an aqueous solution of NaHCO$_3$, 1M aqueous solution of citric acid and an aqueous solution of NaCl successively and dried over sodium sulfate. Then, the reaction mixture was evaporated to dryness to give white powder (58.4 g, 0.12 mol). The peptide was further elongated sequentially in the same manner as described above. Reagents used, amounts thereof and the like are shown below.

(3) Synthesis of Boc—Asp(OBn)—Ser(Bn)—Gly—ONb
Product of (2): 58.4 g (0.12 mol)
TFA/CH$_2$Cl$_2$: 200 ml/200 ml
Boc—Asp(OBn): 36.7 g (0.12 mol)
CH$_2$Cl$_2$: 750 ml
DCC: 24.7 g (0.12 mol)
Yield: 67.2 g (0.10 mol)

(4) Synthesis of Boc—D—Leu—Asp(OBn)—Ser(Bn)—Gly—ONb
Product of (3): 67.2 g (0.10 mol)
TFA/CH$_2$Cl$_2$: 200 ml/200 ml
Boc—D—Leu: 21.4 g (0.10 mol)
CH$_2$Cl$_2$: 750 ml
DCC: 20.6 g (0.10 mol)
Yield: 63.6 g (79 mmol)

(5) Synthesis of Boc—Arg(Mts)—D—Leu—Asp(OBn)—Ser(Bn)—Gly—ONb
Product of (4): 63.6 g (79 mmol)
TFA/CH$_2$Cl$_2$: 200 ml/200 ml
Boc—Arg(Mts): 36.0 g (79 mmol)
DMF: 800 ml
DCC: 16.3 g (79 mmol)
HOBt: 10.8 g (80 mmol)
Yield: 49.7 g (43 mmol)

(6) Synthesis of Boc—Arg(Mts)—D—Leu—Asp(OBn)—Ser(Bn)—Gly

The product of (5) (11.44 g, 10 mmol) was dissolved in 90% acetic acid (300 ml), added with Zn powder (32.7 g, 0.5 mol) and stirred for 3 hours at 0° C. After removing the Zn powder by filtration, the filtrate was concentrated under reduced pressure, made acidic with citric acid and extracted with ethyl acetate. The ethyl acetate layer was dried over sodium sulfate, concentrated under reduced pressure and added with ether to give white powder (6.86 g, 6.8 mmol).

Amino Acid Analysis (nmol/50 μl)
Arg: 2.3055
D—Leu: 2.2380
Asp: 2.1065
Ser: 2.0314
Gly: 2.4707
MS: (M+H$^+$)

2. Condensation of Triethylenetetramine and Peptide fragment

Boc—Arg(Mts)—D—Leu—Asp(OBn)—Ser(Bn)—Gly (4.04 g, 4.0 mmol) was dissolved in DMF (20 ml), added with DCC (0.83 g, 4.0 mmol) and HOBt (0.54 g, 4.0 mmol) with ice cooling and stirred for 1 hour. The reaction mixture was added with triethylenetetramine (0.14 g, 0.96 mmol) dissolved in DMF (20 ml), stirred for 3 hours with ice cooling and further stirred overnight at room temperature. After removing urea, the reaction mixture was concentrated under reduced pressure, and the residue was recrystallized from ethyl acetate to give the objective compound in the protected form (1.13 g)

Deprotection of the protected compound was carried out in the same manner as used in Example 74 to obtain (Arg—D—Leu—Asp—Ser—Gly)$_4$ triethylenetetramide (0.47 g, 0.21 mmol).

Amino Acid Analysis (nmol/50 μl)
Arg: 4.1419
D—Leu: 4.0203
Asp: 4.1202
Ser: 3.6501
Gly: 4.2725
MS: (M+H$^+$) 2259

EXAMPLE 32

Synthesis of Compound 80

Compound 80 was synthesized by following Route 3 below.

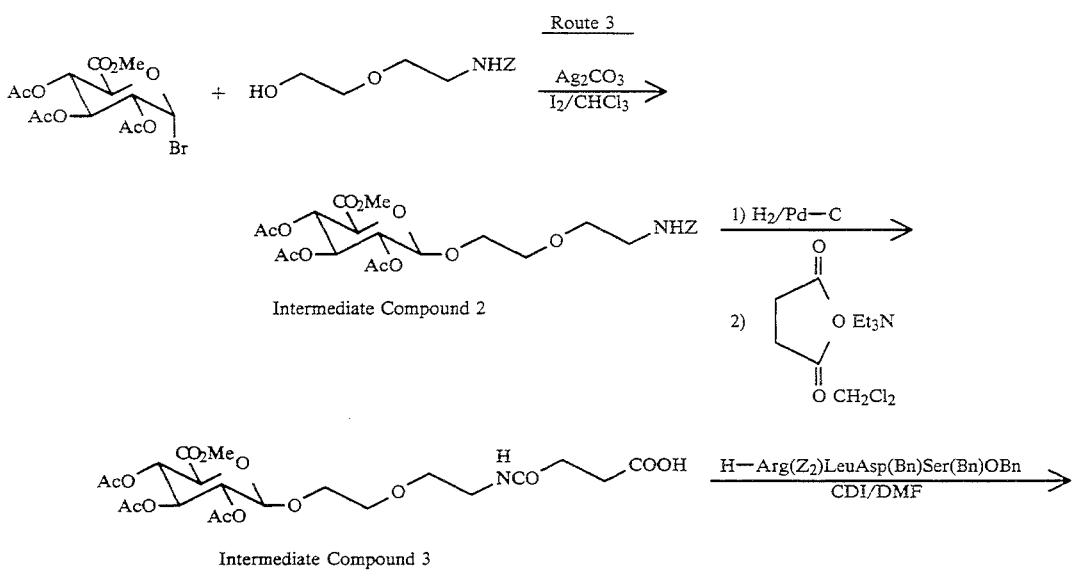

Intermediate Compound 3

-continued
Route 3

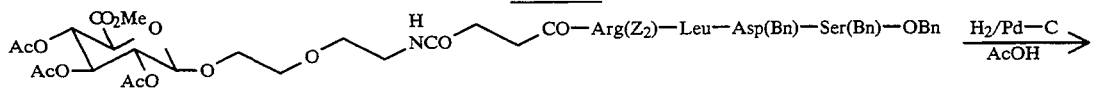

Intermediate Compound 4 (SEQ ID NO: 1)

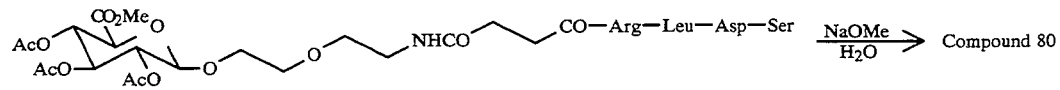

Intermediate Compound 5 (SEQ ID NO: 1)

(a) Synthesis of Arg(Z$_2$)—Leu—Asp(OBn)—Ser-(OBn$_2$)

Compound (1e) of Example 1 (7.0 g, 6.2 mmol) dissolved in methylene chloride (30 ml) was added with trifluoroacetic acid (30 ml) and stirred for 1 hour at room temperature. After the completion of the reaction, the solvent was evaporated and the residue was dissolved in chloroform. The chloroform layer was washed with saturated aqueous solution of NaHCO$_3$ and saturated saline solution successively, dried on anhydrous sodium sulfate and concentrated under reduced pressure. The residue was recrystallized from ether to obtain the Boc-eliminated compound (6.3 g, quantitative). FAB-MS: (M+H)$^+$ 1028.

(b) Synthesis of Intermediate Compound 2

A mixture comprising 2-(2-N-benzyloxycarbonylaminoethoxy)ethanol (7.2 g, 30 mmol), silver carbonate (12 g), Drylite (40 g) and dry chloroform not containing alcohol (100 ml) was stirred for 1 hour while shielded from light to eliminate moisture in the mixture. The mixture was added with iodine (4 g), then added with a solution of (2,3,4-tri-O-acetyl-α-D-glucopyranosyl bromide)-uronate methyl ester (8 g, 20 mmol, prepared according to the method of Y. A. Hassan, J. Carbohydrates Nucreosides Nucreotides, 4, p 77 (1977) in chloroform (50 ml) over more than 30 minutes and stirred for 30 hours at room temperature. The reaction mixture was filtered through a Celite layer to eliminate insoluble components, and the celite layer was washed with chloroform. The filtrate and the washing liquor were combined and washed with water and saturated saline solution, dried over anhydrous sodium sulfate and concentrated under reduced pressure to obtain an oily product. This product was purified by silica gel column chromatography (eluent: chloroform) to give 8.9 g of the desired Intermediate Compound 2 as a colorless oil. Yield: 80%, FAB-MS: (M+H)$^+$ 556, (M+Na)$^+$ 578.

(c) Synthesis of Intermediate Compound 3

Intermediate Compound 2 (5.4 g, 9.7 mmol) was dissolved in methanol (100 ml), added with 10% palladium/carbon (300 mg) and stirred for 13 hours at room temperature under hydrogen atmosphere. After the completion of the reaction, the catalyst was removed by filtration thorough a Celite layer and the Celite layer was washed with methanol. The filtrate and the washing liquor were combined and concentrated under reduced pressure to give an amine compound (4.1 g) as a colorless oily product.

The amine compound was dissolved in methylene chloride (50 ml), added with triethylamine (1.02 g, 10 mmol), and added with succinic anhydride (980 mg, 9.8 mmol) with ice cooling. After stirring the reaction mixture at room temperature for 1 hour, the reaction was stopped by adding a proper amount of water. The water layer was separated from the organic layer and extracted with chloroform. The combined chloroform was washed with water and saturated saline solution, dried over anhydrous sodium sulfate and concentrated under reduced pressure to obtain 5.0 g of the objective Intermediate Compound 3 quantitatively. FAB-MS: (M+H)$^+$ 552.

(d) Synthesis of Intermediate Compound 4

Intermediate Compound 3 (1.04 g, 2 mmol) was dissolved in dry DMF (1 ml) and added with a solution of CDI (330 mg, 2 mmol) in dry DMF (10 ml) with ice cooling. The reaction mixture was stirred for 1 hour with ice cooling and added with a solution of the Boc-eliminated compound of (a) (2.06 g, 2 mmol) in DMF (25 ml). The reaction mixture was stirred for 2 hours with ice cooling and further 20 hours while allowed to warm up to room temperature, and then the solvent was evaporated under reduced pressure. The residue was recrystallized from ether to give 2.3 g of the objective Intermediate Compound 4 as colorless powder. Yield: 75%, FAB-MS: (M+H)$^+$ 1531.

(e) Synthesis of Intermediate Compound 5

Intermediate Compound 4 (1.1 g, 0.7 mmol) was dissolved in acetic acid (30 ml), added with 10% palladium/carbon (100 mg) and stirred for 18 hours at room temperature under hydrogen atmosphere. The catalyst was removed by filtration through a Celite layer and the Celite layer was washed with acetic acid. The filtrate and the washing liquor were combined and concentrated under reduced pressure. The residue was dissolved in a small amount of water and lyophilized to give 690 mg of Intermediate Compound 5 as colorless powder. Yield: 96.7%, FAB-MS: (M+H)$^+$ 993.

(f) Synthesis of Compound 80

Intermediate Compound 5 (650 mg, 0.65 mmol) was dissolved in water (20 ml), added with sodium methoxide powder (180 mg, 3.3 mmol) and stirred for 4 hours at room temperature. After the completion of the reaction, the reaction mixture was neutralized with diluted acetic acid and concentrated under reduced pressure. The residue was dissolved in a small amount of water, purified by gel permeation chromatography using Sephadex G-10 and lyophilized to give 440 mg of Compound 80 as colorless amorphous solid. Yield: 80%, FAB-MS: (M+H)$^+$ 854.

EXAMPLE 33

Synthesis of 6-O-carboxymethyl-N-acetylchitooligosaccharide

6-O-carboxymethylchitin (CM-chitin, carboxymethylation degree: 0.8, deacetylation degree: 0, 6 g) was dissolved in pure water (600 ml) by stirring for a day, added with egg lysozyme (EC 3.2.1.17, 1 g) and shaken for 2 days at 37° C. The reaction mixture was concentrated under reduced pressure and dialyzed against pure water using Spectrapore 6 (MWCO 2000). The outer liquor was lyophilized to give 3 g of 6-O-carboxymethyl-N-acetylchitooligosaccharide mixture. The obtained mixture was fractionated by ion-exchange chromatography (DEAE cellulose) to give 6-O-carboxymethyl-N-acetylchitohexaose (0.35 g), 6-O-carboxymethyl-N-acetylchitopentaose (0.3 g) and 6-O-carboxymethyl-N-acetylchitotetraose (0.3 g)

EXAMPLE 34

Synthesis of Compounds 87 to 91

Compounds 87 to 91 were prepared by using, as starting materials, 4-nitrophenyl-N-acetyl-β-glucosaminide, 4-nitrophenyl-di-N-acetyl-β-chitobiose, 4-nitrophenyl-di-N-acetyl-β-chitotriose, 4-nitrophenyl-α-D-glucopyranoside and 4-nitrophenyl-α-D-maltotrioside, which are commercially available from Seikagaku Kogyo Co., Ltd. and Boeringer Mannheim & Yamanouchi Co., Ltd. As the representative examples of the synthesis of Compounds 87 to 91, syntheses of Compounds 87 and 90 are described below.

(a) Synthesis of Compound 87

Compound 87 was synthesized by following Route 4 below.

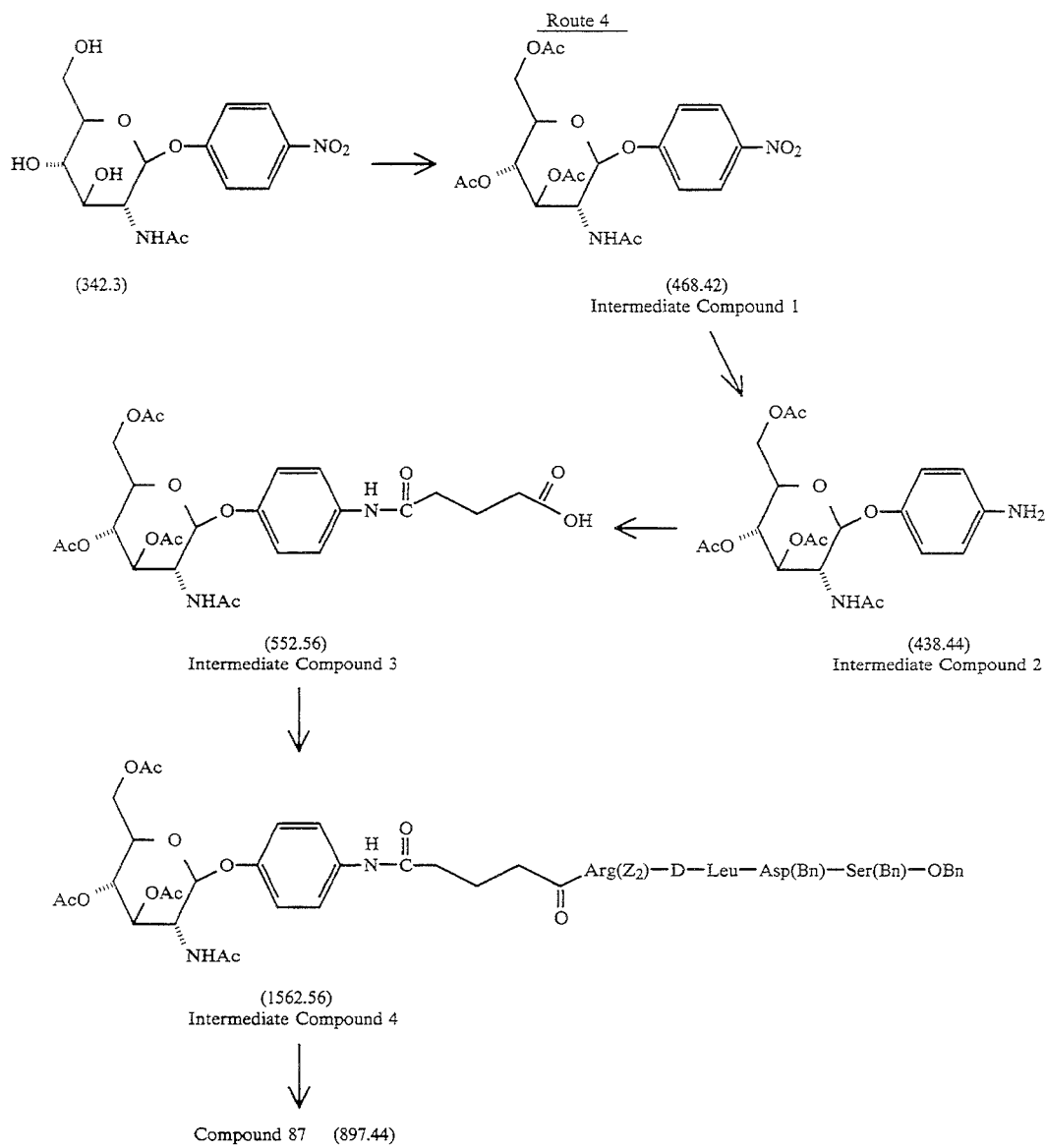

4-nitrophenyl-N-acetyl-β-glucosaminide (3.4 g, 0.01 mol) was added to acetic anhydride (50 ml) and pyridine (100 ml), stirred for 16 hours at room temperature and treated in a conventional manner to give white powder. This was repeatedly precipitated in ether/hexane to give 3.8 g of Intermediate Compound.1.

Intermediate Compound 1 (3.0 g, 0.0064mol) was dissolved in ethyl acetate (100 ml) and added with 10% palladium/carbon (0.3 g) and hydrogenolysis was carried out for 6 hours under hydrogen atmosphere. After removing the catalyst by filtration, the filtrate was concentrated to give 2.7 g of the objective Intermediate Compound 2 as an amorphous product. Because of unstability of this product, it was used in the next step without purification.

Intermediate Compound 2 (2.5 g, 0.0057mol) was dissolved in pyridine (50 ml), added with glutaric anhydride (684 mg, 0.006 mol) and catalytic amount of dimethylaminopyridine and warmed for 14 hours in a water bath at 50° C. After a conventional post-treatment, the resulted residue was purified by silica gel column chromatography (eluent: chloroform/methanol=30/1) to give 2.1 g of the objective Intermediate Compound 3 as powder.

Intermediate Compound 3 (2.0 g, 0.0036 mol) and carbonyldiimidazole (640 mg, 0.004 mol) were dissolved in dry tetrahydrofuran (40 ml) and cooled at 0° C. Boc-eliminated Compound 2 described in Example 2 (4.1 g, 0.004 mol), which has a free amino group, was dissolved in dry DMF (10 ml), cooled and added to the solution of Intermediate Compound 3 dropwise. The reaction mixture was stirred for 16 hours at room temperature and treated in a conventional manner. The resulted residue was purified by silica gel column chromatography (eluent: chloroform/methanol=20/1) to give 4.8 g of the objective Intermediate Compound 4.

Intermediate Compound 4 (2.0 g, 0.0013 mol) was dissolved in ethanol (20 ml), added with 1N NaOH aqueous solution (10 ml) and stirred for 8 hours at room temperature. After neutralization with 1N HCl, the solvent was evaporated and the residue was dried intensively. The residue was dissolved in dry DMF (15 ml), added with sulfur trioxide/trimethylamine complex (500 mg, 0.0036 mol) and stirred for 20 hours at room temperature. After confirming the disappearance of the starting materials by TLC, the reaction mixture was added with a proper amount of saturated $NaHCO_3$ aqueous solution to stop the reaction and neutralized. After evaporating a major part of the solvent, the residue was crystallized with ether, washed with water and dried to give a sulfate ester compound. This product was dissolved in acetic acid (20 ml), added with 10% Pd/C (100 mg) and stirred for 40 hours at room temperature under hydrogen atmosphere. The catalyst was removed by filtration through a Celite layer, the Celite layer was washed with water. The filtrate and the washing water were combined and concentrated under reduced pressure. The residue was dissolved in a small amount of water, purified by gel permeation chromatography using Sephadex G-10 and lyophilized to give 710 mg of Compound 87 as colorless powder. FAB-MS: $(M-H)^+$ 998

Compounds 88 and 89 were prepared in the same manner as described above. FAB-MS data of those compounds are shown below.

| Compound 88 | $(M - H)^-$ | 1387 |
| Compound 89 | $(M - H)^-$ | 700 |

(b) Synthesis of Compound 90

Compound 90 was prepared by following Route 5 below

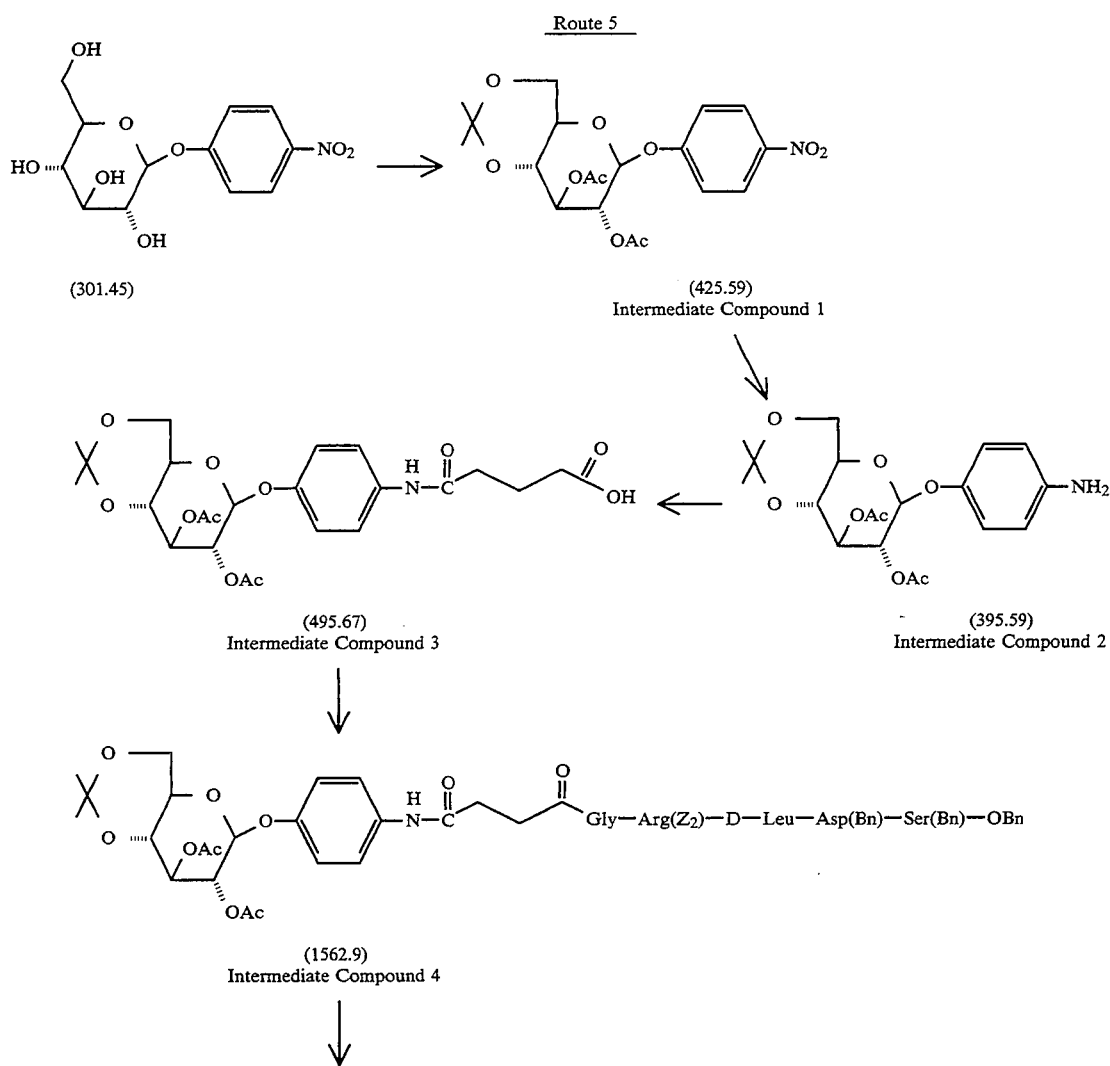

Route 5

(301.45)

(425.59)
Intermediate Compound 1

(495.67)
Intermediate Compound 3

(395.59)
Intermediate Compound 2

(1562.9)
Intermediate Compound 4

-continued
Route 5

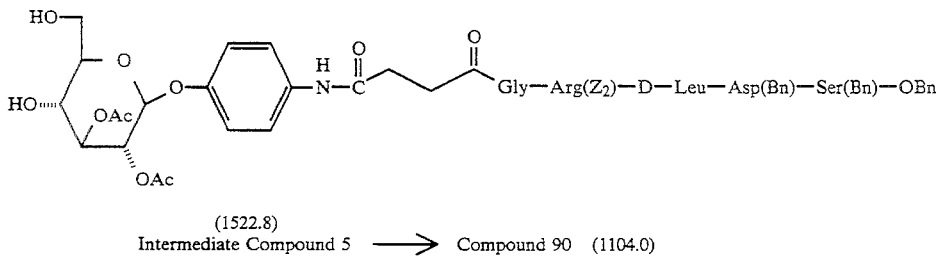

(1522.8)
Intermediate Compound 5 ⟶ Compound 90 (1104.0)

Commercially available 4-nitrophenyl-α-D-glucopyranoside (20 g, 0.066 mol) and dimethoxypropane (24 ml) were dissolved in DMF (400 ml), added with catalytic amount of camphorsulfonic acid and stirred for 16 hours. This reaction mixture was added with acetic anhydride (50 ml) and pyridine (100 ml) and stirred for 24 hours. After removing the excess reagents and the solvent under reduced pressure, the residue was distributed between saturated saline solution and ethyl acetate and repeatedly extracted with ethyl acetate. The organic layer was washed with 5% aqueous hydrochloric acid and saturated saline solution and dried over anhydrous sodium sulfate. After evaporating the solvent, the residue was purified by silica gel chromatography (eluent: ethyl acetate/hexane=1/1) to give 14 g of the objective Intermediate Compound 1.

Intermediate Compound 1 (10 g, 0.023 mol) was dissolved in ethyl acetate (400 ml) and added with 10% Pd/C (0.3 g) to carry out hydrogenolysis for 24 hours. Then, the reaction mixture was filtered and the solvent was evaporated from the filtrate to give the objective Intermediate Compound 2 (9.1 g) as an amorphous product. After confirming the absorbance of amino acids by IR spectra (KBr) (ν 3300-2950 cm$^{-1}$), Intermediate Compound 2 was used in the next step without purification because of its instability.

Intermediate Compound 2 (7.0 g, 0.018 mol) was dissolved in a mixed solvent of chloroform (50 ml) and pyridine (8 ml), added with succinic anhydride (2.2 g, 0.02 mol) and stirred for 2 hours at room temperature. The reaction mixture was treated in a conventional manner, and resulted residue was purified by silica gel column chromatography (eluent: chloroform/methanol=6:1) to give 5.9 g of the objective Intermediate Compound 3 as a slightly yellow amorphous product.

The totally protected t—Boc—Gly—Arg—D—Leu—Asp—Ser was prepared by bonding the Boc-eliminated Compound 2 (1.36 g, 1.32 mmol) obtained by the method described in Example 3 with t—Boc—Gly (0.23 g, 1.32 mmol) by a conventional method (DCC/HOBt method).

Intermediate Compound 3 (1.03 g, 0.002 mol) and carbonyldiimidazole (400 mg, 0.0025 mol) were dissolved in dry tetrahydrofuran (40 ml) and cooled at 0° C. The above-obtained protected peptide of which t—Boc group had been preliminarily eliminated to have a free amino group (2.0 g, 0.002 mol) were dissolved in dry DMF (10 ml) and added to the solution of Intermediate compound 3 dropwise with cooling. Then, the reaction mixture was stirred for 16 hours at room temperature and treated in a conventional manner. The resulted residue was purified by silica gel column chromatography (eluent:chloroform/methanol=20/1) to give 1.8 g of the objective Intermediate Compound 4.

Intermediate Compound 4 (0.78 g, 0.0005 mol) was added to acetic acid containing 85% water (20 ml) and stirred for 5 hours at room temperature. After the completion of the reaction, the solvent was evaporated under reduced pressure to give 0.73 g of the objective Intermediate Compound 5. The structure of this compound was confirmed by the disappearance of the peaks of methyl groups in the acetonide moiety, δ 1.38 (3H, singlet), 1.61 (3H, singlet) in 1H-NMR (solvent: CDCl$_3$,) and the mass spectra. FAB MS (M+H)+ 1523.

Intermediate Compound 5 (0.7 g, 0.00046 mol) was dissolved in dry DMF (15 ml), added with sulfur trioxide/trimethylamine complex (417 mg, 0.003 mmol) and stirred for 20 hours at room temperature. After confirming the disappearance of the starting materials by TLC, the reaction mixture was added with a proper amount of saturated NaHCO$_3$ aqueous solution to stop the reaction, neutralized, added with 1N NaOH aqueous solution (5 ml) and further stirred for 2 hours. After evaporating a major part of the solvent, the residue was crystallized with ether and the crystals ware washed with water and dried to give a sulfate ester compound. This ester compound was dissolved in acetic acid (20 ml), added with 10% Pd/C (100 mg) and stirred for 40 hours at room temperature under hydrogen atmosphere. The catalyst was removed by filtration through a Celite layer and the Celite layer was washed with water. The filtrate and the washing water were combined and concentrated under reduced pressure. The residue was dissolved in a small amount of water and purified by silica gel permeation chromatography using Sephadex G-10 and lyophilized to give 280 mg of the objective Compound 90 as colorless powder. FAB-MS: (M−H)− 1103

Compound 91 was prepared in the same manner as described above. FAB MS: (M−H)− 1399

EXAMPLE 35

Synthesis of Compound 94

6-O-Carboxymethyl-N-Acetylchitohexaose Carrying —Asp—Arg—Leu—Asp—Ser (SEQ ID NO:13)

6-O-carboxymethyl-N-acetylchitohexaose (0.5 g) was dissolved in pure water, added with WSC (0.37 g) and stirred for 1 hour. Then, the reaction mixture was added with Asp—Arg—Leu—Asp—Ser (1.0 g) and stirred for a day. After concentrating the (SEQ ID NO:13) reaction mixture under reduced pressure, the residue was washed with ether and purified with an ion-exchange resin, Amberlite IRA-93 and Sephadex G-50 to give 0.6 g of the objective compound.

Amino Acid Analysis (nmol/50 μl)
Asp: 2.00
Arg: 0.98
Leu: 0.95

Ser: 0.78

EXAMPLE 36

Synthesis of Compound 95

6-O-Carboxymethyl-N-Acetylchitopantaose Carrying —Asp—Arg—D—Leu—Asp—Ser

Compound 95 was prepared in the same manner as in Example by using 6-O-carboxymethyl-N-acetyl-chitopantaose and Asp—Arg—D—Leu—Asp—Ser.

Amino Acid Analysis (nmol/50 μl)
Asp: 2.00
Arg: 0.87
D—Leu: 0.86
Ser: 0.72

EXAMPLE 37

Synthesis of Compound 96

6-O-Carboxymethyl-N-Acetylchitohexaose Carrying —Gly—Arg—Phe—Asp—Ser (SEQ ID NO:10)

Compound 96 was prepared in the same manner as in Example 35 by using 6-O-carboxymethyl-N-acetyl-chitohexaose and Gly—Arg—Phe—Asp—Ser.

Amino Acid Analysis (nmol/50 μl)
Gly: 0.91
Arg: 0.92
Phe: 0.94
Ser : 0.82
Asp: 1.00

EXAMPLE 38

Synthesis of Compound 97

6-O-Carboxymethyl-N-Acetylchitotetraose Carrying —Asp—Arg—D—Phe—Asp—Ser

Compound 97 was prepared in the same manner as in Example 35 by using 6-O-carboxymethyl-N-acetyl-chitotetraose and Asp—Arg—D—Phe—Asp—Ser.

Amino Acid Analysis (nmol/50 μl)
Asp: 2.00
Arg: 1.02
D—Phe: 0.99
Ser: 0.83.

EXAMPLE 39

Synthesis of 6-O-Sulfated-Carboxymethyl-N-Acetylchitooligosaccharide Mixture 6-O-sulfated carboxymethylchitin (SCM-chitin, sulfated degree: 0.6, carboxymethylation degree: 0.4, 5.3 g) was prepared according to the method of Tokura et al., Jpn. J. Cancer Res., 80, p 866 (1989).

The obtained 6-O-sulfated-carboxymethylchitin (5 g) was dissolved in pure water (500 ml) by stirring for a day, added with egg lysozyme (EC 3.2.1.17, 1 g) and shaken for 2 days at 37° C. The reaction mixture was concentrated under reduced pressure and dialyzed against pure water using Spectrapore 6 (MWCO 2000). The outer liquor was lyophilized to give 3.5 g of 6-O-sulfated-carboxymethyl-N-acetylchitooligosaccharide mixture.

EXAMPLE 40

Synthesis of Compound 98

6-O-Sulfated-Carboxymethyl-N-Acetylchitooligosaccharide Carrying —Asp—Arg—Leu—Asp—Ser (SEQ ID NO:13)

6-O-sulfated-carboxymethyl-N-acetylchitooligosaccharide (0.5 g) was dissolved in pure water, added with WSC (0.2 g) and stirred for 1 hour. Then, the reaction mixture was added with Asp—Arg—Leu—Asp—Ser (1.0 g) and stirred for a day. After concentrating the reaction mixture under reduced pressure, the residue was washed with ether and purified with an ion-exchange resin, Amberlite IRA-93 and Sephadex G-50 to give 0.3 g of the objective compound.

Amino Acid Analysis (nmol/50 μl)
Asp: 2.00
Arg: 0.96
Leu: 0.96
Ser: 0.81

EXAMPLE 41

Synthesis of Compound 99

6-O-Sulfated-Carboxymethyl-N-Acetylchitooligosaccharide Carrying —Asp—Arg—D—Leu—Asp—Ser Compound 99 was prepared in the same manner as in Example 40 by using Asp—Arg—D—Leu—Asp—Ser.

Amino Acid Analysis (nmol/50 μl)
Asp: 2.00
Arg: 0.92
D—Leu: 0.95
Ser: 0.73

EXAMPLE 42

Synthesis of Compound 100

6-O-Sulfated Carboxymethyl-N-Acetylchitooligosaccharide Carrying —Gly—Arg—Phe—Asp—Ser (SEQ ID NO:10)

Compound 99 was prepared in the same manner as in Example 40 by using Gly—Arg—Phe—Asp—Ser (SEQ ID NO:10).

Amino Acid Analysis (nmol/50 μl)
Gly: 1.04
Arg: 1.12
Phe: 0.94
Asp: 1.00
Ser: 0.84

EXAMPLE 43

Synthesis of Compound 101

6-O-Sulfated-Carboxymethyl-N-Acetylchitooligosaccharide Carrying —Asp—Arg—D—Phe—Asp—Ser Compound 101 was prepared in the same manner as in Example 40 by using Asp—Arg—D—Phe—Asp—Ser.

Amino Acid Analysis (nmol/50 μl)
Asp: 2.00
Arg: 1.11
Phe: 0.98
Ser: 0.69

EXAMPLE 44

Synthesis of Compound 105

CM-Chitin Carrying —Arg—Leu—Asp—Ser (SEQ ID NO:1)

CM-chitin (Viscosity: 9 cps (1% solution, 20° C.), etherification degree: 0.78, deacetylation degree: 0.5, available from Yaizu Suisan Kagaku Kogyo Co., Ltd., 0.30 g) was dissolved in phosphate buffer (pH 7.4), added with a solution of water-soluble DCC (1-ethyl-3-(dimethylaminopropyl)-carbodiimide, 128 mg) in phosphate buffer (2.6 ml) while maintained at 0° C. and allowed to react for 1.5 hours. Then, the reaction mixture was added with the peptide, Arg—Leu—Asp—Ser (SEQ ID NO:1) (400 mg), dissolved in phosphate buffer (8 ml) and allowed to react overnight at 4° C. The reaction solution was packed in a Visking tube, purified by dialysis against deionized water and then pure water to eliminate low molecular weight compounds and lyophilized. Yield: 0.24 g.

The structure of the product was confirmed by IR and amino acid analysis.

Amino Acid Analysis (nmol/50 μl)
Glucosamine: 20.5558
Arg: 2.0556
Leu: 2.1352
Asp: 1.9854
Ser: 1.8792

Introduction rate of peptide fragment was determined from the ratio of the concentration of arginine residue to that of glucosamine according to the following relation and found to be about 10%.

Introduction rate=[Arg]/[Glucosamine]×100

IR: Stretching vibration of amidocarbonyl (C=O) 1652 cm$^{-1}$

EXAMPLE 45

Synthesis of Compound 106

Succinylated CM-Chitin Carrying —Gly—Arg—D—Leu—Asp—Ser

CM-chitin (20.0 g), the same as used in Example 44, was dissolved in 1% triethylamine solution (100 ml), added with succinic anhydride (34.0 g) and 4-dimethylaminopyridine (2.00 g) and stirred for 24 hours. After the completion of the reaction, the reaction solution was poured into a large excess of acetone to precipitate the succinylated CM-chitin. The recovered precipitates were washed with a large amount of methanol and then with ether and dried in vacuo. Yield: 22.40 g.

The succinylated CM-chitin (0.30 g) was dissolved in phosphate buffer (pH 7.4) and added with a solution of water-soluble DCC (1-ethyl-3-(dimethylaminopropyl)-carbodiimide, 128 mg) in phosphate buffer (2.6 ml) while maintained at 0° C. and allowed to react for 1.5 hours. Then, the reaction mixture was added with the peptide, Gly—Arg—D—Leu—Asp—Ser (400 mg), dissolved in phosphate buffer (8 ml) and allowed to react overnight at 4° C. The reaction solution was packed in a Visking tube, purified by dialysis against deionized water and then pure water to eliminate low molecular weight compounds and lyophilized. Yield: 0.26 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 23.6218
Arg: 2.3622
D—Leu: 2.1253
Asp: 2.2391
Ser: 2.0031

IR: Stretching vibration of amidocarbonyl (C=O) 1652 cm$^{-1}$

EXAMPLE 46

Synthesis of Compound 107

Maleyl Derivative of CM-Chitin Carrying —Asp—Arg—D—Ile—Asp—Ser—NHCH$_3$

CM-chitin (20.0 g) and maleic anhydride (36.6 g) were reacted in the same manner as used in Example 45 to obtain maleyl derivative of CM-chitin (21.60 g).

The maleyl derivative of CM-chitin was dissolved in phosphate buffer (pH 7.4) and covalently bonded with the peptide fragment in the same manner as used in Example 45. Yield: 0.33 g.

The structure of the product was confirmed by IR and amino acid analysis. By the amino acid analysis, the introduction rate of the peptide fragment was found to be about 11%.

Amino Acid Analysis (nmol/50 μl)
Glucosamine: 28.4956
Arg: 3.1345
Thr: 2.7751
Asp: 5.4426
Ser: 2.5694
D—Ile: 2.6120

IR: Stretching vibration of amidocarbonyl (C=O) 1648 cm$^{-1}$

EXAMPLE 47

Synthesis of Compound 108

Phthaloyl Derivative of CM-Chitin Carrying —Asp—D—Arg—Nle—Asp—Ser

CM-chitin (20.0 g) and phthalic anhydride (50.0 g) were reacted in the same manner as used in Example 45 to obtain phthaloyl derivative of CM-chitin (22.31 g).

The phthaloyl derivative of CM-chitin (0.30 g) was dissolved in phosphate buffer (pH 7.4) and covalently bonded with Asp—D—Arg—Nle—Asp—Ser in the same manner as used in Example 45. Yield: 0.44 g.

The structure of the product was confirmed by IR and amino acid analysis. By amino acid analysis, the introduction rate of the peptide fragment was found to be about 12%.

Amino Acid Analysis (nmol/50 μl)
Glucosamine: 19.1856
D—Arg: 1.1023
Nle: 1.2231
Asp: 1.0937
Ser: 1.0632

IR: Stretching vibration of amidocarbonyl (C=O) 1652 cm$^{-1}$

EXAMPLE 48

Synthesis of Compound 109

Itaconyl Derivative of CM-Chitin Carrying —Arg—Leu—Asp—Ser (SEQ ID NO:1)

CM-chitin (20.0 g) and Itaconic anhydride (38.0 g) were reacted in the same manner as used in Example 45 to obtain Itaconyl derivative of CM-chitin (21.45 g).

The Itaconyl derivative of CM-chitin (0.30 g) was dissolved in phosphate buffer (pH 7.4) and covalently bonded with Arg—Leu—Asp—Ser in the same manner as used in Example 45. Yield: 0.36 g.

The structure of the product was confirmed by IR and amino acid analysis. By the amino acid analysis, the introduction rate of the peptide fragment was found to be about 9%.

Amino Acid Analysis (nmol/50 μl)
Glucosamine: 35.2316
Arg: 3.1708
Leu: 3.2511
Asp: 3.1005
Ser: 2.8862
IR: Stretching vibration of amidocarbonyl (C=O) 1650 cm$^{-1}$

EXAMPLE 49

Synthesis of Compound 110

CM-Chitin Carrying
—Gly—Arg—D—Phe—Asp—Ser—Pro

Compound 110 was prepared in the same manner as in Example 44 by using Gly—Arg—D—Phe—Asp—Ser—Pro (460 mg) as the peptide fragment. Yield: 0.36 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 15.3319
Arg: 1.5332
Gly: 1.4132
Asp: 1.3468
Ser: 1.1132
Pro: 1.3078
D—Phe: 1.5810
IR: Stretching vibration of amidocarbonyl (C=O) 1654 cm$^{-1}$

EXAMPLE 50

Synthesis of Compound 111

CM-Chitin Carrying
—Gly—Asp—D—Phg—Asp—Thr—NH$_2$

Compound 111 was prepared in the same manner as in Example by using Gly—Asp—D—Phg—Asp—Thr—NH$_2$ (460 mg) as the peptide fragment. Yield: 0.36 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 17.6368
Arg: 1.8166
Gly: 1.8243
Asp: 3.7468
Ser: 1.6112
D—Phg: 1.7134
IR: Stretching vibration of amidocarbonyl (C=O) 1658 cm$^{-1}$

EXAMPLE 51

Synthesis of Compound 112

Succinylated CM-Chitin Carrying
—(Arg—D—Leu—Asp—Ser)$_2$

Compound 112 was prepared in the same manner as in Example 45 by using (Arg—D—Leu—Asp—Ser)$_2$ (460 mg) as the peptide fragment. Yield: 0.31 g.

The structure of the product was confirmed by IR and amino acid analysis. By the amino acid analysis, the introduction rate of the peptide fragment was found to be about 12%.

Amino Acid Analysis (nmol/50 μl)
Glucosamine: 25.1913
Arg: 6.0459
D—Leu: 5.9883
Asp: 5.8996
Ser: 5.7398
IR: Stretching vibration of amidocarbonyl (C=O) 1654 cm$^{-1}$

EXAMPLE 52

Synthesis of Compound 113

Sulfated CM-Chitin Carrying
—Gly—Arg—Nle—Asp—Ser—NHCH$_3$ (SEQ ID NO:9)

CM-chitin (etherification degree: 0.50, deacetylation degree: 0.05) was sulfated according to the method of Tokura et al., Jpn. J. Cancer Res., 80, p 866–872 (1989) and Cancer Res., 50, p 3631–3637 (1990) and covalently bonded to Gly—Arg—Nle—Asp—Ser—NHCH$_3$ (SEQ ID NO:9) fragment in the same manner as used in Example 44. Yield: 0.36 g.

The structure of the product was confirmed by IR and amino acid analysis. By the amino acid analysis, the introduction rate of the peptide fragment was found to be about 12%.

Amino Acid Analysis (nmol/50 μl)
Glucosamine: 33.1569
Arg: 3.9780
Gly: 3.9251
Asp: 3.6053
Ser: 3.4921
Nle: 3.5548
IR: Stretching vibration of amidocarbonyl (C=O) 1650 cm$^{-1}$

EXAMPLE 53

Synthesis of Compound 114

Sulfated CM-Chitin Carrying
—Gly—D—Arg—Leu—Asp—Ser

The peptide fragment Gly—D—Arg—Leu—Asp—Ser (460 mg) and the sulfated CM-chitin as described in Example 52 were covalently bonded in the same manner as used in Example 44 to give Compound 114. Yield: 0.35 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 25.1515
D—Arg: 2.5152
Gly: 2.4134
Asp: 2.4251

Ser: 2.1111
Leu: 2.5631
IR: Stretching vibration of amidocarbonyl (C=O) 1655 cm$^{-1}$

EXAMPLE 54

Synthesis of Compound 115

Sulfated Succinylated CM-Chitin Carrying
—Arg—Phe—Asp—Ser—NH—iso—C$_3$H$_7$

Succinylated CM-chitin was sulfated in the same manner as used in Example 52 and covalently bonded with the peptide fragment Arg—Phe—Asp—Ser—NH—iso—C$_3$H$_7$ (SEQ ID NO:3) to give Compound 115. Yield: 0.37 g.

The structure of the product was confirmed by IR and amino acid analysis. By the amino acid analysis, the introduction rate of the peptide fragment was found to be about 14%.

Amino Acid Analysis (nmol/50 μl)
Glucosamine: 18.6932
Arg: 2.6170
Phe: 2.7739
Asp: 2.5931
Ser: 2.2168
IR: Stretching vibration of amidocarbonyl (C=O) 1654 cm$^{-1}$

EXAMPLE 55

Synthesis of Compound 116

Sulfated Succinylated CM-Chitin Carrying
—Arg—D—Leu—Asp—Ser—Pro—NHC$_2$H$_5$

Succinylated CM-chitin was sulfated in the same manner as used in Example 52 and covalently bonded with the peptide fragment Arg—D—Leu—Asp—Ser—Pro—NHC$_2$H$_5$ to give Compound 116. Yield: 0.37 g.

The structure of the product was confirmed by IR and amino acid analysis. By the amino acid analysis, the introduction rate of the peptide fragment was found to be about 14%.

Amino Acid Analysis (nmol/50 μl)
Glucosamine: 18.6932
Arg: 2.6170
D—Leu: 2.7739
Asp: 2.5931
Ser: 2.2168
Pro: 2.2916
IR: Stretching vibration of amidocarbonyl (C=O) 1654 cm$^{-1}$

EXAMPLE 56

Synthesis of Compound 117

Chondroitin Sulfate Carrying
—Gly—D—Arg—Leu—Asp—Ser—NH—isoC$_3$H$_7$

Chondroitin sulfate (viscosity: 9 cps (1% solution, 20° C.), etherification degree: 0.78, available from Yaizu Suisan Kagaku Kogyo Co., Ltd., 0.30 g) was dissolved in phosphate buffer (pH 7.4), added with a solution of 1-ethyl-3-(dimethylaminopropyl)-carbodiimide (128 mg) in phosphate buffer (2.6 ml) and allowed to react 1.5 hours. Then, the reaction mixture was added with the peptide Gly—D—Arg—Leu—Asp—Ser—NHisoC$_3$H$_7$ (400 mg) dissolved in phosphate buffer (8 ml) and allowed to react overnight at 4° C. The reaction solution was packed in a Visking tube, purified by dialysis against deionized water and then pure water to eliminate low molecular weight compounds and lyophilized. Yield: 0.24 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 20.5558
D—Arg: 2.0556
Gly: 2.1352
Asp: 1.9854
Ser: 1.8792
Leu: 1.9790
IR: Stretching vibration of amidocarbonyl (C=O) 1652 cm$^{-1}$

EXAMPLE 57

Synthesis of Compound 118

Succinylated Chondroitin Sulfate Carrying
—D—Arg—Phe—Asp—Ser

The chondroitin sulfate (20.0 g) the same as used in Example 56 was dissolved in 1% triethylamine solution (10 ml), added with succinic anhydride (34.0 g) and 4-dimethylaminopyridine (2.00 g) and stirred at room temperature for 24 hours. After the completion of the reaction, the reaction solution was poured into a large excess of acetone to precipitate the succinylated chondroitin sulfate. The recovered precipitates were washed with large amount of methanol and then with ether and dried in vacuo. Yield: 22.40 g.

The succinylated chondroitin sulfate (0.30 g) was dissolved in phosphate buffer (pH 7.4), added with a solution of 1-ethyl-3-(dimethylaminopropyl)-carbodiimide (128 mg) in phosphate buffer (2.6 ml) while maintained at 0° C. and allowed to react 1.5 hours. Then, the reaction mixture was added with the peptide D—Arg—Phe—Asp—Ser (400 mg) dissolved in phosphate buffer (8 ml) and allowed to react overnight at 4° C. The reaction solution was packed in a Visking tube, purified by dialysis against deionized water and then pure water to eliminate low molecular weight compounds and lyophilized. Yield: 0.26 g.

The structure of the product was confirmed by IR and amino acid analysis. By the amino acid analysis, the introduction rate of the peptide fragment was found to be about 10%.

Amino Acid Analysis (nmol/50 μl)
Glucosamine: 23.6218
D—Arg: 2.3622
Phe: 2.1253
Asp: 2.2391
Ser: 2.0031
IR: Stretching vibration of amidocarbonyl (C=O) 1652 cm$^{-1}$

EXAMPLE 58

Synthesis of Compound 119

Maleyl Derivative of Chondroitin Sulfate Carrying
—Arg—D—Leu—Asp—Ser

Chondroitin sulfate (20.00 g) the same as used in Example 56 was reacted with maleic anhydride (36.6 g) in the same manner as used in Example 57 to obtain maleyl derivative of chondroitin sulfate (21.60 g). This maleyl derivative of chondroitin sulfate (0.30 g) was dissolved in phosphate buffer (pH 7.4) and covalently bonded with the peptide fragment, Arg—D—Leu—Asp—Ser, in the same manner as used in Example 45. Yield: 0.33 g.

The structure of the product was confirmed by IR and amino acid analysis. By the amino acid analysis, the introduction rate of the peptide fragment was found to be about 11%.

Amino Acid Analysis (nmol/50 μl)
Glucosamine: 28.4956
Arg: 3.1345
D—Leu: 2.7751
Asp: 2.7213
Ser: 2.5694
IR: Stretching vibration of amidocarbonyl (C=O) 1648 cm$^{-1}$

EXAMPLE 59

Synthesis of Compound 120

Trimellityl Derivative of Chondroitin Sulfate Carrying —Glu—Arg—Phg—Asp—Ser

Chondroitin sulfate (20.00 g) the same as used in Example 56 was reacted with trimellitic anhydride (64.9 g) in the same manner as used in Example 57 to obtain trimellityl derivative of chondroitin sulfate (23.74 g). This trimellityl derivative of chondroitin sulfate (0.30 g) was dissolved in phosphate buffer (pH 7.4) and covalently bonded with the peptide fragment, Glu—Arg—Phg—Asp—Ser, in the same manner as used in Example 45. Yield: 0.37 g.

The structure of the product was confirmed by IR and amino acid analysis. By the amino acid analysis, the introduction rate of the peptide fragment was found to be about 14%.

Amino Acid Analysis (nmol/50 μl)
Glucosamine: 18.7612
Arg: 2.6266
Glu: 2.7899
Asp: 2.5532
Ser: 2.2689
Phg: 2.2449
IR: Stretching vibration of amidocarbonyl (C=O) 1656 cm$^{-1}$

EXAMPLE 60

Synthesis of Compound 121

Succinyl Derivative of Chondroitin Sulfate Carrying —(Arg—D—Leu—Asp—Ser)$_2$

By using (Arg—D—Leu—Asp—Ser)$_2$ (460 mg) as the peptide fragment, Compound 121 was prepared in the same manner as used in Example 57. Yield: 0.31 g.

The structure of the product was confirmed by IR and amino acid analysis. By the amino acid analysis, the introduction rate of the peptide fragment was found to be about 12%.

Amino Acid Analysis (nmol/50 μl)
Glucosamine: 25.1913
Arg: 6.0459
D—Leu: 5.9883
Asp: 5.8996
Ser: 5.8798
IR: Stretching vibration of amidocarbonyl (C=O) 1654 cm$^{-1}$

EXAMPLE 61

Synthesis of Compound 122

Succinyl Derivative of Chondroitin Sulfate Carrying —(Arg—D—Leu—Asp—Ser)$_5$

By using (Arg—D—Leu—Asp—Ser)$_5$ (460 mg) as the peptide fragment, Compound 122 was prepared in the same manner as used in Example 57. Yield: 0.28 g.

The structure of the product was confirmed by IR and amino acid analysis. By the amino acid analysis, the introduction rate of the peptide fragment was found to be about 15%.

Amino Acid Analysis (nmol/50 μl)
Glucosamine: 23.6811
Arg: 23.0108
D—Leu: 21.0993
Asp: 20.3332
Ser: 21.0728
IR: Stretching vibration of amidocarbonyl (C=O) 1656 cm$^{-1}$

EXAMPLE 62

Synthesis of Compound 123

Cyanurate Derivative of Polyethylene Glycol (Arg—Leu—Asp—Ser)$_2$

Compound 123 was prepared by following Route 6 below.

Route 6

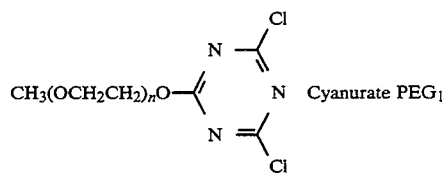

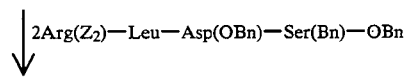

-continued

Route 6

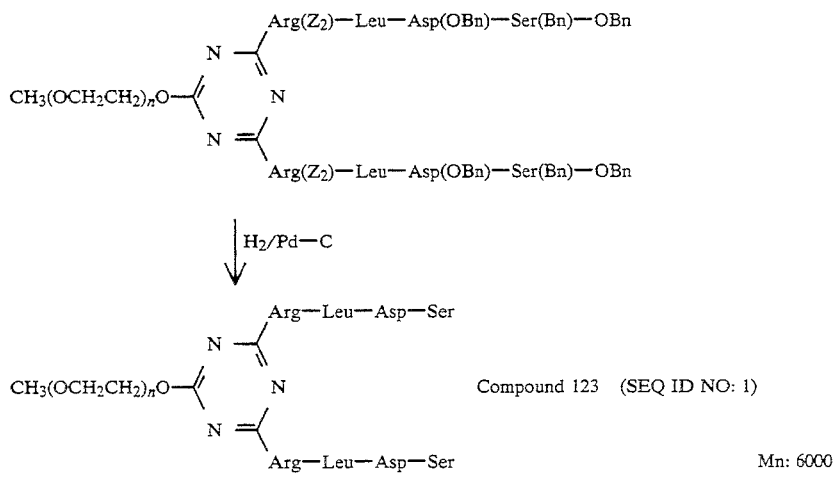

(1) Synthesis of cyanurate derivative of polyethylene glycol (Cyanurate PEG$_1$)

Polyethylene glycol monomethyl ether having an average molecular weight of 5000 (10 g, 2 mmol) was sufficiently dried, added with toluene (100 ml), sodium carbonate (5 g) and cyanuric chloride (1.1 g, 6 mmol) and stirred at 80° C. for 120 hours. After allowing the reaction solution to cool down to room temperature, the solution was filtered and the filtrate was added with hexane to be crystallized. The crystals were further purified by recrystallization from a solvent system of toluene/acetone/hexane to give white powder of Cyanyrate PEG$_1$ (7 g).

(2) Synthesis of Cyanurate PEG$_1$ (Arg—Leu—Asp—Ser)$_2$ (SEQ ID NO:1)$_2$

Boc—Arg(Z$_2$)—Leu—Asp(OBn)—Ser(Bn)—OBn (SEQ ID NO:1) (1.14 g, 1 mmol) was dissolved in methylene chloride (10 ml), added with trifluoroacetic acid (10 ml) and stirred for 30 minutes at room temperature. After evaporating the solvent under reduced pressure, the residue was added with chloroform (100 ml), washed several times with 1N NaHCO$_3$ aqueous solution (100 ml) and saturated saline solution (100 ml) and dried over anhydrous sodium sulfate. The sodium sulfate was removed by filtration and the filtrate was concentrated under reduced pressure to give white powder. This white powder was mixed with Cyanurate PEG$_1$ (2.5 g), triethylamine (0.1 g) and chloroform (50 ml) and stirred for 24 hours at room temperature. Then, the mixture was purified by gel filtration (Sephadex LH-60) to give 3.1 g of Cyanurate PEG$_1$ (Arg(Z$_2$)—Leu—Asp(OBn)—Ser(Bn)—OBn)$_2$.

This protected peptide derivative (3.1 g) was dissolved in acetic acid (50 ml) and added with 10% Pd/C (1.0 g) and hydrogenolysis was carried out for 24 hours at room temperature under hydrogen atmosphere at atmospheric pressure. After removing the catalyst by filtration through a Celite layer and evaporating the solvent under reduced pressure, the residue was purified by gel filtration (Sephadex LH-60) to give 2.5 g of Cyanurate PEG$_1$ (Arg—Leu—Asp—Ser)$_2$.

Amino Acid Analysis (nmol/50 μl)
Arg: 1.0326
Leu: 0.9574
Asp: 0.9811
Ser: 0.9209
Number Average Molecular Weight: 6000

EXAMPLE 63

Synthesis of Compound 124

Cyanurate Derivative of Polyethylene Glycol-(Arg—D—Leu—Asp—Ser)

Compound 124 was prepared by following Route 7 below.

Route 7

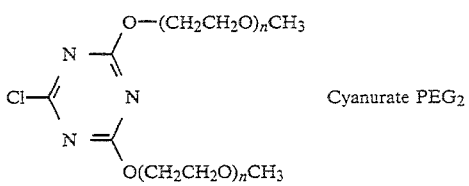

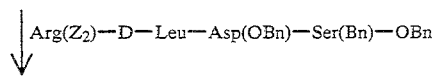

Route 7

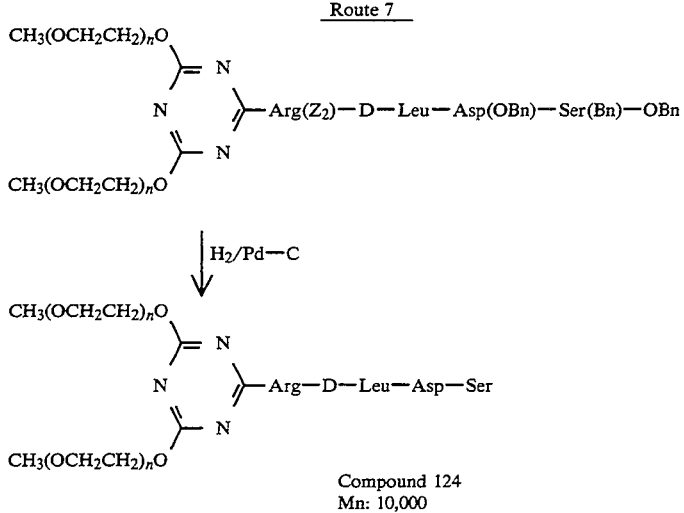

Compound 124
Mn: 10,000

Boc—Arg(Z₂)—D—Leu—Asp(OBn)—Ser(Bn)—OBn (1.14 g, 1 mmol) was dissolved in methylene chloride (10 ml), added with trifluoroacetic acid (10 ml) and stirred for 30 minutes at room temperature. After evaporating the solvent under reduced pressure, the residue was added with chloroform (100 ml), washed several times with 1N NaHCO₃ aqueous solution (100 ml) and saturated saline solution (100 ml) and dried over anhydrous sodium sulfate. The sodium sulfate was removed by filtration and the filtrate was concentrated under reduced pressure to give white powder. This white powder was mixed with cyanurate derivative of polyethylene glycol (Cyanurate PEG₂, available from Seikagaku Kogyo Co., Ltd., 1.25 g), triethylamine (0.1 g) and chloroform (50 ml) and stirred for 24 hours at room temperature, Then, the mixture was purified by gel filtration (Sephadex LH-60) to give 1.79 g of Cyanurate PEG₂-(Arg(Z₂)—D—Leu—Asp(OBn)—Ser(Bn)—OBn).

This protected peptide derivative (1.79 g) was dissolved in acetic acid (50 ml) and added with 10% Pd/C (1.0 g) and hydrogenolysis was carried out for 24 hours at room temperature under hydrogen atmosphere at atmospheric pressure. After removing the catalyst by filtration through a Celite layer and evaporating the solvent under reduced pressure, the residue was purified by gel filtration (Sephadex LH-60) to give 1.34 g of Cyanurate PEG₂-(Arg—D—Leu—Asp—Ser).

Amino Acid Analysis (nmol/50 μl)
Arg: 1.1408
D—Leu: 0.9357
Asp: 0.9412
Ser: 0.9166
Number Average Molecular Weight: 10000

EXAMPLE 64

Synthesis of Compound 125

Polyethylene Oxide Carboxylic Acid Derivative Carrying —Gly—Arg—Leu—Asp—Ser (SEQ ID NO:4)

Boc—Gly—Arg(Z₂)—Leu—Asp(OBn)—Ser(Bn)—OBn (SEQ ID NO:4) (0.63 g, 0.5 mmol) was dissolved in methylene chloride (10 ml), added with trifluoroacetic acid (10 ml) and stirred for 30 minutes at room temperature. After evaporating the solvent under reduced pressure, the residue was added with chloroform (100 ml), washed several times with 1N NaHCO₃ aqueous solution (100 ml) and saturated saline solution (100 ml) and dried over anhydrous sodium sulfate. The sodium sulfate was removed by filtration and the filtrate was concentrated under reduced pressure to give white powder. This white powder was mixed with polyethylene oxide carboxylic acid derivative (PEO Acid #4000, available from Kawaken Fine Chemicals Co., Ltd., 1.0 g), dicyclohexylcarbodiimide (0.12 g, 0.55 mmol) and chloroform (50 ml) and stirred for 24 hours at room temperature. Then, the mixture was purified by gel filtration (Sephadex LH-20, eluent: chloroform/methanol=9/1) to eliminate peptide fragments which were not bonded to the polyethylene glycol derivative. The introduction rate of the peptide fragment to the carboxyl group in the product was determined from the ratio of the intensities of the methylene proton and the aromatic proton in ¹H NMR and found to be about 65%.

This protected-peptide-introduced polyethylene glycol derivative (1 g) was dissolved in ethanol (100 ml) and water (10 ml) and added with 10% Pd/C (1.0 g) and hydrogenolysis was carried out for 24 hours at room temperature under hydrogen atmosphere at atmospheric pressure. After removing the catalyst by filtration through a Celite layer and evaporating the solvent under reduced pressure, the residue was subjected to gel filtration (Sephadex LH-20, eluent: ethanol) to remove the released protective groups and purified by ion-exchange chromatography (DEAE-Sephadex A-25) to give 250 mg of carboxyl derivative of polyethylene glycol-(Gly—Arg—Leu—Asp—Ser) (SEQ ID NO:4).

Amino Acid Analysis (nmol/50 μl)
Gly: 1.0151
Arg: 1.0045
Leu: 0.9897
Asp: 0.9564
Ser: 0.9106
Number Average Molecular Weight: 4900

EXAMPLE 65

Synthesis of Compound 126

Polyethylene Oxide Carboxylic Acid Derivative Carrying —Gly—Arg—Leu—Asp—Ser—Pro—NH$_2$ (SEQ ID NO:15)

Protected peptide, Boc—Gly—Arg(Z$_2$)—Leu—Asp(OBn)—Ser(Bn)—Pro—NH$_2$ was prepared by starting with Boc—Pro—NH$_2$ (SEQ ID NO:15) and sequentially extending each of corresponding amino acids at the N-terminal of the peptide. In the same manner as used in Example 64, PEO Acid #4000 (1.0 g) and the protected peptide (0.6 g, 0.50 mmol) were condensed and subjected to hydrogenolysis to give 310 mg of the objective carboxyl derivative of polyethylene glycol-(Gly—Arg—Leu—Asp—Ser—Pro—NH$_2$) (SEQ ID NO:15)

Amino Acid Analysis (nmol/50 μl)
Gly: 0.9841
Arg: 1.0193
Leu: 0.9417
Asp: 0.9924
Ser: 0.8846
Pro: 0.9511
Number Average Molecular Weight: 5200

Pharmacological Test: Experimental tumor metastasis in lungs, liver and spleen

The tumor metastasis inhibitory activities of the peptide derivatives of the present invention were examined as follows.

Each of the following peptide derivatives according to the present invention, Compounds 1 to 13, 15, 19 to 22, 25, 32, 36, 37, 44, 47, 50, 56-1, 56-4, 59, 65, 68, 70, 73, 76, 77, 80, 84, 87, 89, 90, 94, 96, 99, 101, 103,106, 112, 114, 118 and 121 was mixed with B16-BL6 melanoma cells having a potent metastatic tendency in PBS so that 0.2 ml of the mixture contained 3000, 1000 or 500 μg of the peptide derivative and 5×10$^6$ of B16-BL6 melanoma cells. Then, 0.2 ml of each mixture was intravenously administered to each individual of a group of C57BL/6 female mice consisting of 5 mice. Fourteen days after the administration, the number of melanoma cell colony in lungs was determined and compared with that of the control mice, which were administered with PBS. The results are shown in Table 4 below.

Separately, each of the following peptide derivatives of the present invention, Compound 1, 2, 8, 12, 20, 47, 56, 59, 67, 73 and 85, was mixed with L5178Y ML25 T-lymphoma cells in PBS so that 0.2 ml of the mixture contained 3000 or 1000 μg of the peptide derivative and 4×10$^4$ of the T-lymphoma cells. Then, 0.2 ml of each mixture was intravenously administered to each individual of a group of CDF$_1$(BALB/c×DBA/2) female mice consisting of 5 mice. Fourteen days after the administration, the weights of the livers and the spleens of the mice were determined and compared with those of the control mice. The results are shown in Table 5 below.

For comparison, the peptide fragments known to have tumor metastasis inhibition activity, Arg—Gly—Asp—Ser (SEQ ID NO:16) (Comparison A), Gly—Arg—Gly—Asp—Ser (SEQ ID NO:17) (Comparison B) and (Arg—Gly—Asp)n (n=5) (SEQ ID NO:18) as well as Reference Polymer A were also administered to the mice in the same manner as above.

As seen from the results shown in Tables 4 and 5, the peptide derivatives according to the invention more effectively inhibited the metastases of the tumor cells to the lungs as compared with the conventional adhesive peptide sequences. This clearly shows that the peptide derivatives of the present invention have higher tumor metastasis inhibitory activity than the conventional peptide compounds. In particular, the peptide derivatives of the present invention comprising the peptide sequences modified with the organic groups show high inhibitory activity with a small administration dose, and it means that the enhancement of the activity by the modification with organic groups, which is one of the important object of the present invention, has been successfully achieved.

Further, it was also found that the peptide derivatives of the present invention can exhibit high tumor metastasis inhibitory activity even though the derivatives were administered 5 minutes after the administration of B16-BL6 cells without mixing the derivatives and tumor cells (Table 4, Experiment 2, Compounds 20 and 22). This means that the peptide derivatives of the present invention can exhibit the tumor metastasis inhibitory effect in patients having cancer, when the derivatives are administered to the patients by a proper way such as intravenous injection.

TABLE 4

Inhibitory Effect on Experimental Melanoma Metastasis in Lungs Caused by Injection of B16-BL6 Melanoma Cell

| Compound | Dose (μg) | Number of Colony Average ± SD | (Range) |
|---|---|---|---|
| *Experiment 1* | | | |
| Control (PBS) | — | 116 ± 27 | (84–160) |
| 1 | 3000 | 35 ± 3 | (30–36)** |
| 2 | 3000 | 41 ± 8 | (29–49)** |
| 3 | 3000 | 39 ± 18 | (23–58)** |
| 4 | 3000 | 35 ± 11 | (23–47)** |
| 5 | 3000 | 51 ± 6 | (44–57)** |
| 6 | 3000 | 51 ± 10 | (10–29)** |
| 7 | 3000 | 25 ± 6 | (17–32)** |
| 8 | 3000 | 37 ± 9 | (28–43)** |
| 9 | 3000 | 22 ± 10 | (11–29)** |
| 10 | 3000 | 58 ± 15 | (41–72)* |
| 11 | 3000 | 19 ± 10 | (9–31)** |
| 12 | 3000 | 23 ± 4 | (18–26)** |
| 13 | 3000 | 42 ± 8 | (35–51)** |
| 15 | 3000 | 43 ± 12 | (19–57)** |
| Comparison A | 3000 | 70 ± 8 | (59–78)* |
| Comparison B | 3000 | 50 ± 10 | (35–63)** |
| Comparison C | 1000 | 40 ± 15 | (26–59)* |
| *Experiment 2* | | | |
| Control (PBS) | — | 84 ± 11 | (48–85) |
| 19 | 1000 | 21 ± 8 | (12–24)** |
| 20+ | 1000 | 20 ± 9 | (18–27)** |
| 21 | 1000 | 16 ± 13 | (2–33)** |
| 22+ | 1000 | 19 ± 8 | (13–29)** |
| 25 | 1000 | 30 ± 6 | (23–38)** |
| 32 | 1000 | 24 ± 5 | (18–30)** |
| Comparison A | 1000 | 62 ± 9 | (54–73)* |
| Comparison B | 1000 | 40 ± 10 | (29–51)* |
| Comparison C | 1000 | 23 ± 9 | (13–29)* |

+compounds 20 and 22 were administered 5 minutes after the administration of the myeloma cells.

| | | | |
|---|---|---|---|
| *Experiment 3* | | | |
| Control (PBS) | — | 145 ± 30 | (114–180) |
| 36 | 500 | 46 ± 6 | (39–57)** |
| 37 | 500 | 27 ± 11 | (13–39)** |
| 44 | 500 | 66 ± 15 | (49–79)** |
| Comparison A | 3000 | 92 ± 14 | (76–129)* |
| Comparison B | 1000 | 89 ± 18 | (71–98)* |
| Comparison C | 500 | 68 ± 9 | (58–79)** |
| *Experiment 4* | | | |
| Control (PBS) | — | 116 ± 19 | (98–142) |
| 73 | 500 | 38 ± 7 | (30–44)** |
| 76 | 500 | 48 ± 5 | (42–52)** |
| 77 | 500 | 41 ± 6 | (34–48)** |
| 56-1 | 500 | 11 ± 10 | (0–21)** |
| 56-4 | 500 | 19 ± 5 | (13–23)** |

TABLE 4-continued

Inhibitory Effect on Experimental Melanoma Metastasis in Lungs Caused by Injection of B16-BL6 Melanoma Cell

| Compound | Dose (μg) | Number of Colony Average ± SD | (Range) |
|---|---|---|---|
| 59 | 500 | 32 ± 9 | (23–43)** |
| Reference Polymer A | 1000 | 98 ± 26 | (68–126) |
| Comparison A | 3000 | 74 ± 11 | (66–87)* |
| Comparison B | 1000 | 78 ± 8 | (69–88)* |
| Experiment 5 | | | |
| Control (PBS) | — | 91 ± 33 | (65–136) |
| 47 | 1000 | 25 ± 4 | (20–28)* |
| 50 | 1000 | 19 ± 10 | (4–30)** |
| 65 | 1000 | 10 ± 4 | (4–14)** |
| 68 | 1000 | 16 ± 5 | (10–23)** |
| 70 | 1000 | 23 ± 5 | (14–30)* |
| Comparison A | 3000 | 60 ± 4 | (55–67) |
| Comparison B | 1000 | 49 ± 7 | (33–56) |
| Comparison C | 1000 | 39 ± 11 | (18–55)* |
| Experiment 6 | | | |
| Control (PBS) | — | 128 ± 24 | (100–156) |
| 80 | 500 | 36 ± 7 | (27–44)* |
| 84 | 500 | 13 ± 6 | (5–20)** |
| 87 | 500 | 20 ± 9 | (9–28)** |
| 89 | 500 | 29 ± 11 | (16–39)* |
| 90 | 500 | 44 ± 9 | (32–51)* |
| Comparison A | 3000 | 88 ± 20 | (65–112)* |
| Comparison B | 1000 | 76 ± 6 | (65–87)* |
| Comparison C | 500 | 57 ± 12 | (44–71)* |
| Experiment 7 | | | |
| Control (PBS) | — | 85 ± 20 | (64–107) |
| 94 | 500 | 14 ± 3 | (8–16)** |
| 96 | 500 | 9 ± 4 | (3–11)** |
| 99 | 500 | 3 ± 3 | (0–6)** |
| 101 | 500 | 13 ± 6 | (2–22)** |
| 103 | 500 | 24 ± 8 | (14–33)** |
| 106 | 500 | 1 ± 1 | (0–3)** |
| 112 | 500 | 14 ± 7 | (6–23)** |
| 114 | 500 | 21 ± 11 | (10–33)** |
| 118 | 500 | 43 ± 8 | (33–49)* |
| 121 | 500 | 45 ± 11 | (33–59)* |
| Comparison A | 3000 | 51 ± 6 | (45–59)* |
| Comparison B | 1000 | 50 ± 8 | (40–56)* |
| Comparison C | 500 | 44 ± 16 | (28–63)* |

*p < 0.01 when compared with Control t-test
**p < 0.001 when compared with Control in t-test

TABLE 5

Inhibitory Effect on Experimental T-lymphoma Metastasis in Liver and Spleen Caused by Injection of L5178Y ML25 T-lymphoma cell

| Compound | Dose (μg) | Weight (g): Average ± SD (Range) Liver | Spleen |
|---|---|---|---|
| Control (PBS) | — | 4.21 ± 0.49 | 0.28 ± 0.03 |
| 1 | 3000 | 1.29 ± 0.32** | 0.10 ± 0.02** |
| 2 | 3000 | 2.01 ± 0.20** | 0.11 ± 0.02** |
| 8 | 3000 | 1.92 ± 0.20** | 0.11 ± 0.02** |
| 12 | 3000 | 2.67 ± 0.78* | 0.17 ± 0.05* |
| 20 | 1000 | 2.66 ± 0.67* | 0.16 ± 0.06* |
| 47 | 1000 | 2.28 ± 0.54** | 0.14 ± 0.04** |
| 56 | 1000 | 1.88 ± 0.28** | 0.13 ± 0.03** |
| 59 | 1000 | 1.80 ± 0.77** | 0.14 ± 0.04** |
| 67 | 1000 | 1.62 ± 0.52** | 0.12 ± 0.02** |
| 73 | 1000 | 1.95 ± 1.00* | 0.15 ± 0.05* |
| 85 | 1000 | 1.11 ± 0.09** | 0.10 ± 0.02** |
| Comparison A | 1000 | 3.67 ± 1.04 | 0.22 ± 0.03 |
| Comparison B | 1000 | 2.24 ± 0.46** | 0.17 ± 0.03** |
| Reference++ | | 1.09 ± 0.11 | 0.08 ± 0 |

++T-lymphoma cells were not administered.
*p < 0.01 when compared with Control t-test
**p < 0.001 when compared with Control in t-test

Toxicity

In the above in vivo tests, it was confirmed that the peptide derivatives of the present invention have no cytotoxicity against the erythrocyte cells, the spleen cells and the thymus cells of the host mice and no undesirable serum protein coagulation activity.

As described above, the peptide derivatives of the present invention have higher tumor metastasis inhibitory activities as compared with the core sequences of the cell adhesive proteins and suffer almost no problem of toxicity. The structures of the compounds are rather simple and, therefore, the peptide derivatives of the present invention are extremely valuable as pharmaceutical drugs.

What is claimed is:

1. A method for inhibiting tumor metastasis comprising administering in an effective tumor metastasis inhibiting amount to a subject in need thereof a pharmaceutical composition comprising a peptide containing 1 to 20 units of a peptide unit of the following general formula {I} or a pharmaceutically acceptable salt thereof;

{X}—Arg—X—Asp—{Y}    {I} wherein Arg represents L- or D-arginine residue, Asp represents L-aspartic acid residue, X represents L- or D-leucine, D-isoleucine, L- or D-norleucine, L- or D-phenylalanine, D-phenylglycine or D-alanine residue, and {Z} and {Y} each represents an amino acid or a peptide residue, which may be present or absent, selected from glycine, L-serine, L-threonine, L- and D-aspartic acid, L-alanine, L- and D-glutamic acid, L-proline residues and a peptide residue constituted by the foregoing amino acid residues.

2. The method of claim 1 wherein the peptide is an oligopeptide or polypeptide composed of one or more of the peptide sequences of the formula [I] or pharmaceutically acceptable salts thereof, of which carboxyl terminal may be amidated.

3. The method of claim 2 wherein the peptide comprises 2 to 20 units of the peptide sequence of the formula [I] or pharmaceutically acceptable salts thereof.

4. The method of claim 1 which further comprises one or more pharmaceutically acceptable organic groups bonded to said one or more peptide units, wherein said organic groups maintain the water-solubility of said one or more peptide units and do not reduce the biological activity of said one or more peptide units.

5. The method of claim 4 wherein the organic group is selected from;
i) acyl, alkyl and alkylamino groups, which groups may contain —O—, —NH—, —S—, ester bond, amide bond, urethane bond or urea bond, and
ii) groups comprising monosaccharides, oligosaccharides, polysaccharide derivatives, polycarboxylic acids, polyamines, polymers formed from monomers having an ethylenically unsaturated bond, polyethylene glycol, and carboxylic acid derivative of polyethylene oxide, which groups may be bonded to the peptide sequences through an alkylene group or an arylene group, which alkylene and arylene groups may contain —O—, —NH—, —S—, ester bond, amide bond, urethane bond or urea bond.

6. The method of claim 5 wherein the organic group is bonded to the peptide sequences at the amino terminals of the peptide sequences and the carboxyl terminals of the peptide sequences are represented by —OR$_a$ or —NR$_b$R$_c$, where each of R$_a$, R$_b$ and R$_c$ represents a hydrogen atom or a linear or cyclic alkyl group and R$_b$ and R$_c$ may be bonded together to form a ring structure.

7. The method of claim 6 wherein the organic group has at least one group selected from a carboxylate group, sulfonate group, sulfate group and phosphate group.

8. The method of claim 5 wherein the organic group is bonded to the peptide sequences at the carboxyl terminals of the peptide sequences and the amino terminals have a hydrogen atom or substituted or unsubstituted acyl group.

9. The method of claim 8 wherein the organic group has at least one group selected from a carboxylate group, sulfonate group, sulfate group and phosphate group.

10. The method of claim 5 wherein the peptide is a polypeptide comprising 2 to 20 units of the peptide sequence of the formula, the amino terminal of the polypeptide having a substituted or unsubstituted acyl group and the carboxyl terminal of the polypeptide having a substituted or unsubstituted linear or cyclic alkylamino group.

11. The method of claim 5 wherein the peptide comprises 1 to 5 units of the peptide sequence of the formula [I] or pharmaceutically acceptable salt thereof and the organic group is selected from those derived form polycarboxylic acids or polyamines.

12. The method of claim 5 wherein the peptide comprises 1 to 10 units of the peptide sequence of the formula [I] or pharmaceutically acceptable salt thereof and the organic group is selected from those derived form polyethylene glycol.

13. The method of claim 5 wherein the peptide comprises 1 to 10 units of the peptide sequence of the formula [I] or pharmaceutically acceptable salt thereof and the organic group is selected from those derived form monosaccharides, oligosaccharides and polysaccharide derivatives.

14. The method of claim 13 wherein the organic group of those derived form monosaccharides, oligosaccharides and polysaccharide derivatives has at least one group selected from a carboxylate group, sulfonate group, sulfate group and phosphate group on the sugar chain thereof.

15. A compound comprising 1 to 20 units of a peptide unit of the following general formula {I} or a pharmaceutically acceptable salt thereof;

{Z}—Arg—X—Asp—{Y}    {I} wherein Arg represents L- or D-arginine residue, Asp represents L-aspartic acid residue, X represents L- or D-leucine, D-isoleucine, L- or D-norleucine, D-phenylalanine or D-phenylglycine residue, and {Z} and {Y} each represents an amino acid or a peptide residue, which may be present or absent, selected from glycine, L-serine, L-threonine, L- and D-aspartic acid, L-alanine, L- and D-glutamic acid, L-proline residues and a peptide residue constituted by the foregoing amino acid residues.

16. The compound of claim 15 which has an average molecular weight of from 1,000 to 100,000.

17. The compound of claim 15 which is an oligopeptide or polypeptide composed of one or more of the peptide sequences of the formula [I] or pharmaceutically acceptable salts thereof, of which carboxyl terminal may be I amidated.

18. The compound of claim 17 which comprises 2 to 20 units of the peptide sequence of the formula [I] or pharmaceutically acceptable salt thereof.

19. The compound of claim 15 wherein said compound consists of one or more of the peptide units represented by the general formula [I] and one or more of pharmaceutically acceptable organic groups bonded to the units, which maintain the water-solubility of the compound and do not reduce the biological activity of the compound.

20. The compound of claim 19 wherein the organic group is selected from;
i) acyl, alkyl and alkylamino groups, which groups may contain —O—, —NH—, —S—, ester bond, amide bond, urethane bond or urea bond, and
ii) groups comprising monosaccharides, oligosaccharides, polysaccharaide derivatives, polycarboxylic acids, polyamines, polymers formed from monomers having an ethylenically unsaturated bond, polyethylene glycol, and carboxylic acid derivative of polyethylene oxide, which groups may be bonded to the peptide sequences through an alkylene group or an arylene group, which alkylene and arlylene groups may contain —O—, —NH—, —S—, ester bond, amide bond, urethane bond or urea bond.

21. The compound of claim 20 wherein the organic group is bonded to the peptide sequences at the amino terminals of the peptide sequences and the carboxyl terminals of the peptide sequences are represented by —OR$_a$ or —NR$_b$R$_c$, where each of R$_a$, R$_b$ and R$_c$ represents a hydrogen atom or a linear or cyclic alkyl group and R$_b$ and R$_c$ may be bonded together to form a ring structure.

22. The compound of claim 21 wherein the organic group has at least one group selected from a carboxylate group, sulfonate group, sulfate group and phosphate group.

23. The compound of claim 20 wherein the organic group is bonded to the peptide sequences at the carboxyl terminals of the peptide sequences and the amino terminals have a hydrogen atom or substituted or unsubstituted acyl group.

24. The compound of claim 23 wherein the organic group has at least one group selected from a carboxylate group, sulfonate group, sulfate group and phosphate group.

25. The compound of claim 20 which is a polypeptide comprising 2 to 20 units of the peptide sequence of the formula [I] or pharmaceutically acceptable salt thereof, the amino terminal of the polypeptide having a substituted or unsubstituted acyl group and the carboxyl terminal of the polypeptide having a substituted or unsubstituted linear or cyclic alkylamino group.

26. The compound of claim 20 comprising 1 to 5 units of the peptide sequence of the formula [I] or pharmaceutically acceptable salt thereof and the organic group being selected from those derived form polycarboxylic acids or polyamines.

27. The compound of claim 26 wherein the polycarboxylic acids are polymers formed from acrylic acids and methacrylic acids.

28. The compound of claim 26 wherein the polyamines are polymers formed from allylamine.

29. The compound of claim 20 comprising 1 to 10 units of the peptide sequence of the formula [I] or pharmaceutically acceptable salt thereof and the organic group being selected from those derived form polyethylene glycol.

30. The compound of claim 29 the polyethylene glycol has an average molecular weight of from 2,000 to 10,000.

31. The compound of claim 20 comprising 1 to 10 units of the peptide sequence of the formula [I] or pharmaceutically acceptable salt thereof and the organic group being selected from those derived form monosaccharides, oligosaccharides and polysaccharide derivatives.

32. The compound of claim 31 wherein the organic group of those derived form monosaccharides, oligosaccharides and polysaccharide derivatives has at least one group selected from a carboxylate group, sulfonate group, sulfate group and phosphate group on the sugar chain thereof.

---

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Arg   Leu   Asp   Ser
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Arg   Xaa   Asp   Ser
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Arg   Phe   Asp   Ser
    1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly   Arg   Leu   Asp   Ser
    1                             5

( 2 ) INFORMATION FOR SEQ ID NO:5:

( i ) SEQUENCE CHARACTERISTICS:
        ( A ) LENGTH: 5 amino acids (B) TYPE: amino acid
(D) TOPOLOGY: linear (ii) MOLECULE TYPE: peptide (xi) SEQUENCE DESCRIPTION: SEQ ID NO:5:

Arg Arg Leu Asp Ser
1               5

(2) INFORMATION FOR SEQ ID NO:6:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:6:

Glu Arg Leu Asp Ser
1               5

(2) INFORMATION FOR SEQ ID NO:7:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:7:

Asp Arg Phe Asp Ser
1               5

(2) INFORMATION FOR SEQ ID NO:8:

(i) SEQUENCE CHARACTERISTICS:
(A) LENGTH: 16 amino acids
(B) TYPE: amino acid
(D) TOPOLOGY: linear (ii) MOLECULE TYPE: peptide (xi) SEQUENCE DESCRIPTION: SEQ ID NO:8:

Arg Leu Asp Ser Arg Leu Asp Ser Arg Leu Asp Ser Arg Leu Asp Ser
1               5                   10                  15

(2) INFORMATION FOR SEQ ID NO:9:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:9:

Gly Arg Xaa Asp Ser
1               5

(2) INFORMATION FOR SEQ ID NO:10:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:10:

```
      Gly  Arg  Phe  Asp  Ser
      1                   5
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
      Ala  Arg  Leu  Asp  Ser
      1                   5
```

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
      Arg  Ile  Asp  Ser
      1
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
      Asp  Arg  Leu  Asp  Ser
      1                   5
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
      Arg  Leu  Asp  Ser  Arg  Leu  Asp  Ser
      1                   5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
      Gly  Arg  Leu  Asp  Ser  Pro
      1                   5
```

( 2 ) INFORMATION FOR SEQ ID NO:16:

( i ) SEQUENCE CHARACTERISTICS:

(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:16:

Arg Gly Asp Ser
1

(2) INFORMATION FOR SEQ ID NO:17:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:17:

Gly Arg Gly Asp Ser
1               5

(2) INFORMATION FOR SEQ ID NO:18:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:18:

Arg Gly Asp Arg Gly Asp Arg Gly Asp Arg Gly Asp Arg Gly Asp
1               5                   10                  15

* * * * *